(12) United States Patent
Bakos et al.

(10) Patent No.: US 10,206,682 B2
(45) Date of Patent: Feb. 19, 2019

(54) MAGNETIC TISSUE COMPRESSION DEVICE WITH BACKUP MECHANICAL LATCH

(71) Applicant: ETHICON LLC, Guaynabo, PR (US)

(72) Inventors: Gregory J. Bakos, Mason, OH (US); Bethany F. Grant, Scituate, MA (US); John V. Hunt, Cincinnati, OH (US); Daniel W. Price, Loveland, OH (US); Nicholas B. Van Stolk, Cincinnati, OH (US); Frederick E. Shelton, IV, Hillsboro, OH (US)

(73) Assignee: Ethicon LLC, Guaynabo, PR (US)

( * ) Notice: Subject to any disclaimer, the term of this patent is extended or adjusted under 35 U.S.C. 154(b) by 0 days.

(21) Appl. No.: 15/419,086

(22) Filed: Jan. 30, 2017

(65) Prior Publication Data
US 2018/0214150 A1    Aug. 2, 2018

(51) Int. Cl.
*A61B 17/11* (2006.01)
*A61B 17/00* (2006.01)

(52) U.S. Cl.
CPC . *A61B 17/1114* (2013.01); *A61B 2017/00477* (2013.01); *A61B 2017/00876* (2013.01); *A61B 2017/1117* (2013.01); *A61B 2017/1139* (2013.01)

(58) Field of Classification Search
CPC .................... A61B 17/1114; A61B 2017/1139
USPC ... 606/103, 8, 151, 153, 157, 158, 191, 213, 606/216, 217
See application file for complete search history.

(56) References Cited

U.S. PATENT DOCUMENTS

| 5,336,233 A | 8/1994 | Chen |
| 6,036,704 A | 3/2000 | Yoon |

(Continued)

FOREIGN PATENT DOCUMENTS

| CN | 202 437 231 U | 9/2012 |
| CN | 105 054 984 A | 11/2015 |

(Continued)

OTHER PUBLICATIONS

U.S. Appl. No. 15/298,816, filed Oct. 20, 2016.
(Continued)

*Primary Examiner* — Pedro Philogene
*Assistant Examiner* — David C Comstock
(74) *Attorney, Agent, or Firm* — Frost Brown Todd LLC

(57) ABSTRACT

A tissue compression device for forming an anastomosis between first and second anatomical structures may include a first device portion having a first magnetic member and a second device portion having a second magnetic member. The magnetic members are configured to magnetically draw together the first and second device portions to compress tissue positioned therebetween. The compression device further includes a latching mechanism configured to couple the first device portion with the second device portion when the device portions are magnetically drawn together. The latching mechanism may include a first latching member extending from the first device portion and a second latching member extending from the second device portion. The latching members are configured to lockingly engage and thereby couple the first device portion with the second device portion.

20 Claims, 25 Drawing Sheets

(56) References Cited

U.S. PATENT DOCUMENTS

| | | | |
|---|---|---|---|
| 8,257,389 B2* | 9/2012 | Chanduszko | A61B 17/0057 606/213 |
| 9,364,238 B2 | 6/2016 | Bakos et al. | |
| 2004/0034377 A1* | 2/2004 | Sharkawy | A61B 17/0057 606/153 |
| 2006/0282106 A1* | 12/2006 | Cole | A61B 17/0057 606/153 |
| 2011/0144560 A1* | 6/2011 | Gagner | A61B 17/1114 604/8 |
| 2011/0295055 A1* | 12/2011 | Albrecht | A61B 5/073 600/37 |
| 2014/0309670 A1* | 10/2014 | Bakos | A61B 17/1114 606/153 |
| 2016/0324523 A1 | 11/2016 | Lukin et al. | |
| 2016/0374682 A1* | 12/2016 | Leonard | A61F 2/064 606/153 |

FOREIGN PATENT DOCUMENTS

| | | |
|---|---|---|
| CN | 105 615 953 A | 6/2016 |
| SU | 1 438 738 A1 | 11/1988 |
| WO | WO 81/00668 A1 | 3/1981 |

OTHER PUBLICATIONS

U.S. Appl. No. 15/419,102, filed Jan. 30, 2017.
U.S. Appl. No. 15/419,132, filed Jan. 30, 2017.
U.S. Appl. No. 15/419,151, filed Jan. 30, 2017.
U.S. Appl. No. 61/697,845, filed Sep. 7, 2012.
International Search Report and Written Opinion dated Jun. 6, 2018 for Application No. PCT/IB2018/050400, 16 pgs.

* cited by examiner

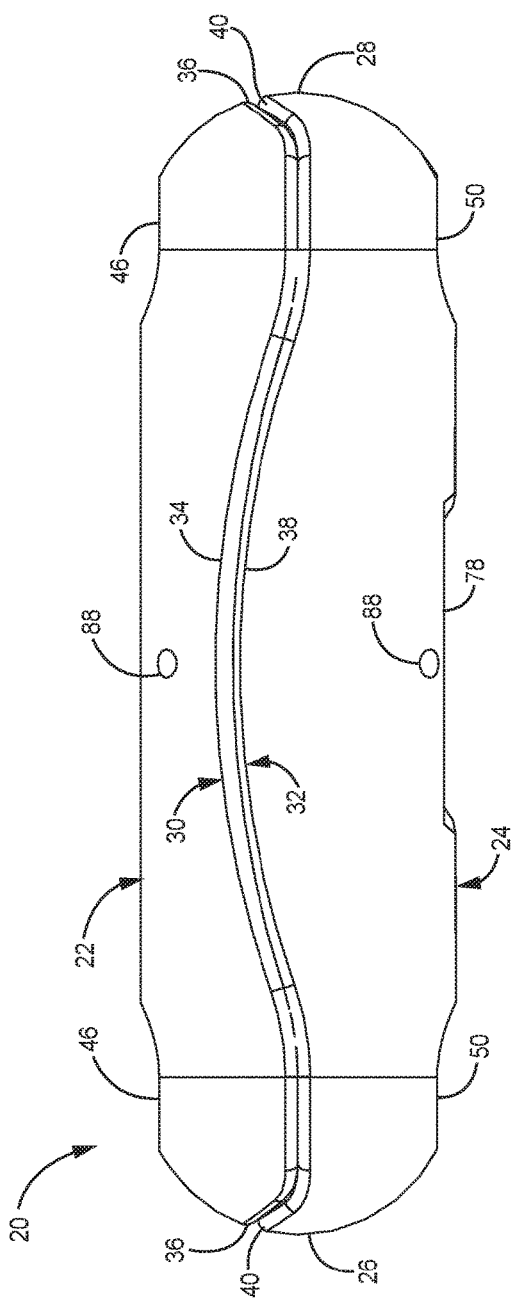
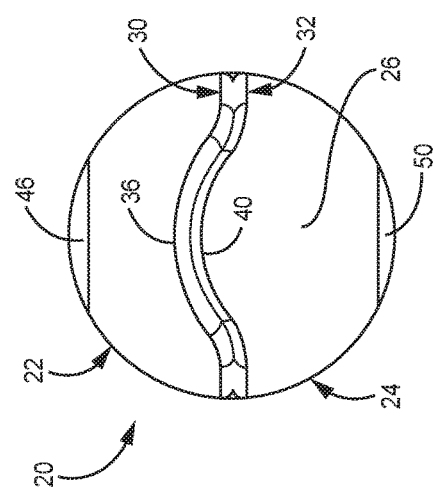
FIG. 4A
FIG. 4B

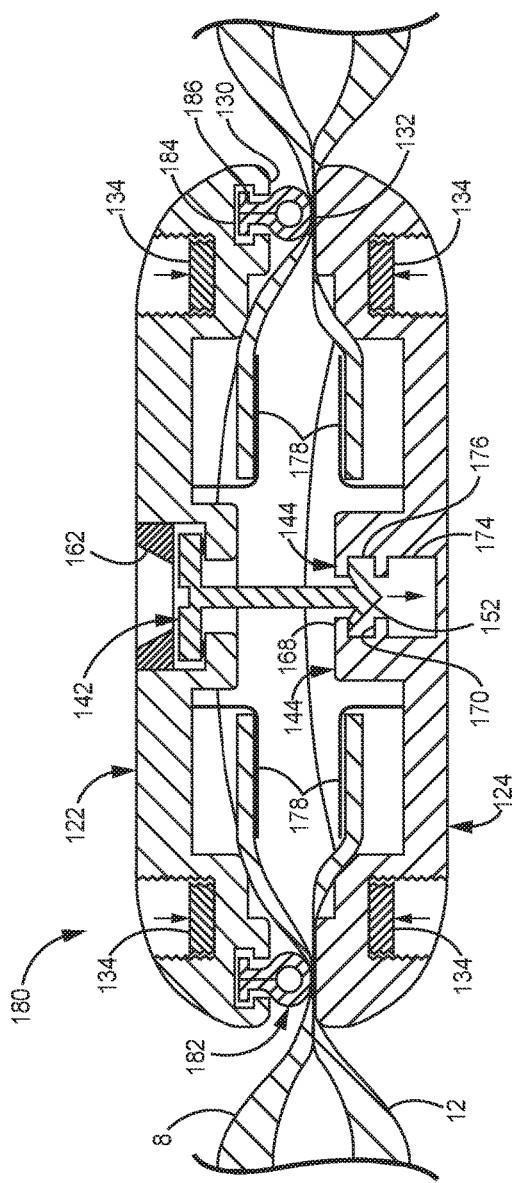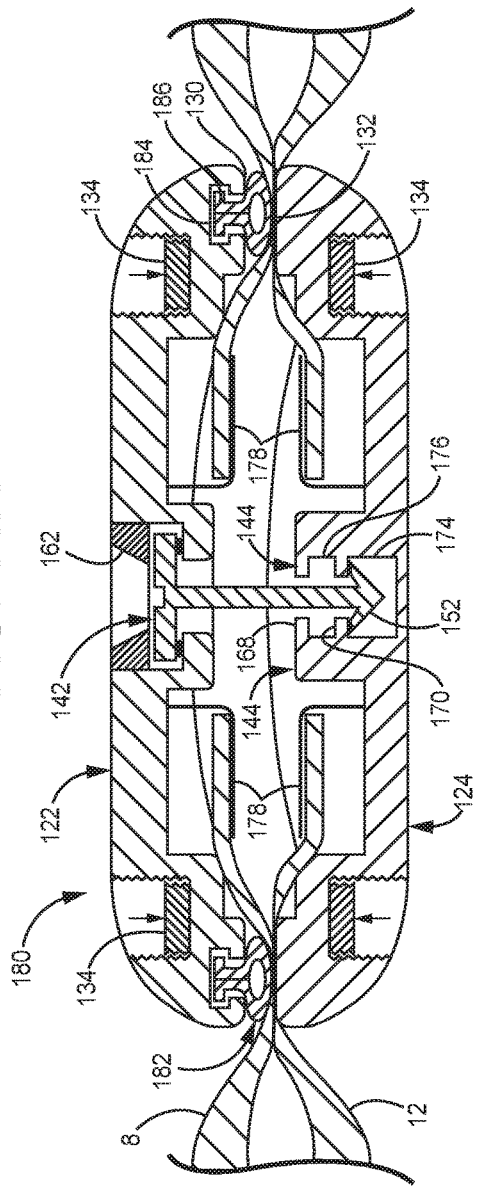

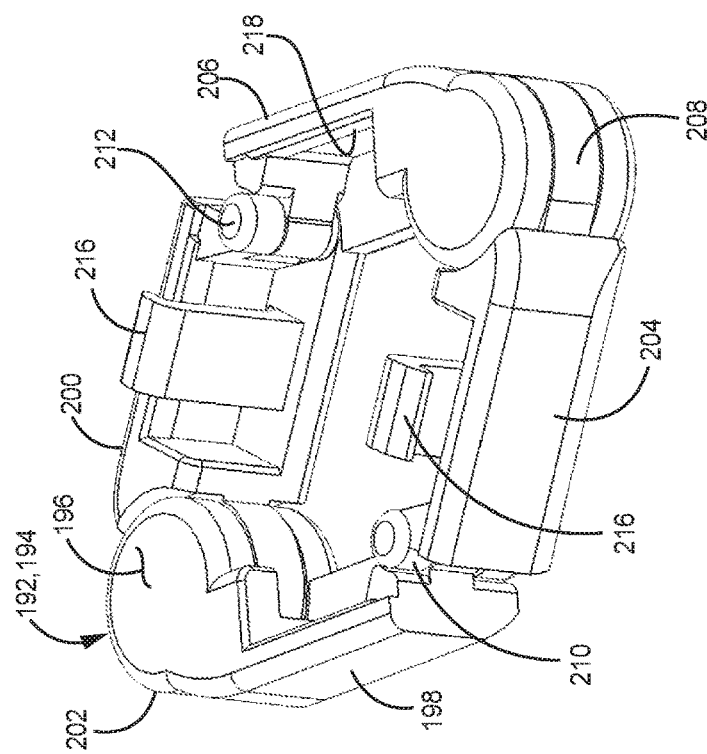
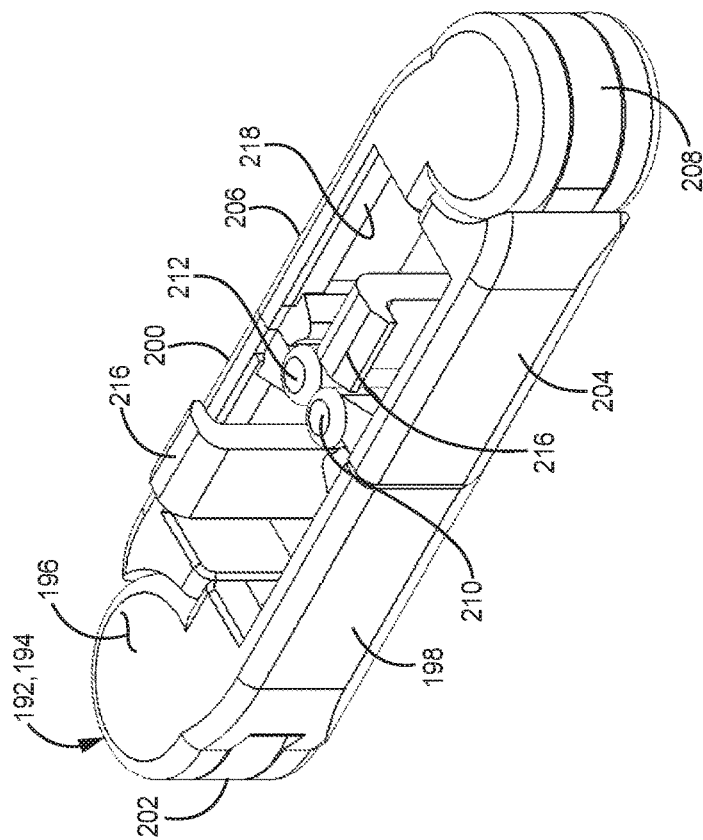

MAGNETIC TISSUE COMPRESSION DEVICE WITH BACKUP MECHANICAL LATCH

BACKGROUND

In some instances, it may be desirable to provide a side-to-side anastomosis between two naturally occurring lumens within a patient's body. By way of example only, it may be desirable to provide an anastomosis between two portions of a patient's gastrointestinal tract, such as between the patient's duodenum and the patient's ileum. In some patients, it may improve glucose control, serve as a treatment for type 2 diabetes, and/or provide other results when the jejunum is diverted by an anastomosis. In such a procedure, a first enterotomy may be formed in the sidewall of the duodenum while a second enterotomy is formed in the sidewall of the ileum. The sidewalls may then be positioned adjacent to each other to form an anastomosis between the portions of the duodenum and the ileum in which the enterotomies are formed, as described in greater detail below. The anastomosis establishes direct fluid communication between the adjacent portions of the duodenum and ileum, enabling at least some nutrient-rich chyme to pass through the anastomosis to travel from the duodenum directly to the ileum without passing through the jejunum. In other variations in which the anastomosis is positioned at other locations within the gastrointestinal tract, some chyme may pass through a shortened portion of the jejunum. In either case, the anastomosis enables accelerated passage of nutrient-rich chyme through the gastrointestinal tract.

One or more devices may be positioned within the first and second enterotomies to hold the sidewalls of the duodenum and ileum together, thereby holding the first and second openings in alignment with each other and maintaining patency through the openings. The device or devices may compress the tissue, which may ultimately result in a serosa-to-serosa adhesion that secures the duodenum sidewall to the ileum sidewall. In addition, tissue captured in the device or devices may eventually necrose, such that the device or devices is/are eventually released into the gastrointestinal tract and subsequently passed through the bowels. Traditional examples of anastomosis devices include Denan's rings and the Murphy button. Examples of anastomosis procedures and associated devices are taught in U.S. Provisional Patent App. No. 61/697,845, entitled "Magnetic Compression Anastomosis Device," filed Sep. 7, 2012, the disclosure of which is incorporated by reference herein; U.S. Pat. No. 9,364,238, entitled "Method and Apparatus for Joining Hollow Organ Sections in Anastomosis," issued Jun. 14, 2016, the disclosure of which is incorporated by reference herein; and U.S. patent application Ser. No. 15/298,816, entitled "Method for Partial Diversion of the Intestinal Tract," filed Oct. 20, 2016, published as U.S. Pub. No. 2017/0035425 on Feb. 9, 2017, the disclosure of which is incorporated by reference herein.

While a variety of anastomosis devices and methods have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements, and in which:

FIG. 4A depicts a side elevational view of the tissue compression device of FIG. 3;

FIG. 4B depicts an end elevational view of the tissue compression device of FIG. 3;

FIG. 14A depicts a side cross-sectional view of another exemplary tissue compression device similar to the device shown in FIG. 9 but additionally including a compressible member arranged between the first and second device halves;

FIG. 14B depicts a side cross-sectional view of the tissue compression device of FIG. 14A, showing compression of the compressible member along with tissue positioned between the first and second device halves as the device halves are magnetically drawn together;

FIG. 17A depicts a perspective view of a device half of the tissue compression device of FIG. 15, shown in a collapsed state;

FIG. 17B depicts a perspective view of a device half of the tissue compression device of FIG. 15, shown in an expanded state:

Figure 1:
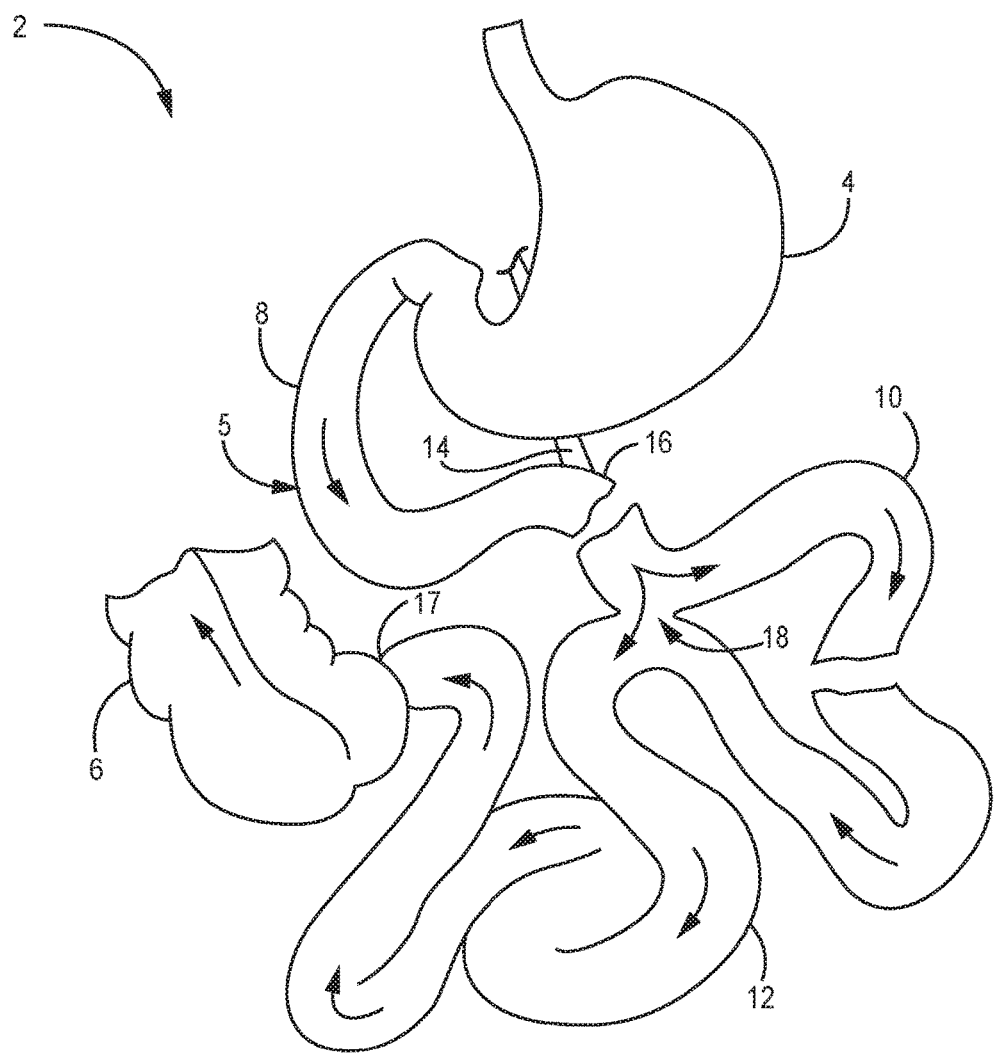
FIG. 1 depicts a diagrammatic view of a portion of a patient's digestive system, showing an exemplary side-by-side anastomosis formed in the small intestine.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Intestinal Anastomosis

As noted above, it may be desirable to provide an anastomosis between two anatomical structures within a patient's body, such as two portions of a patient's gastrointestinal tract. FIG. 1 shows an exemplary portion of a gastrointestinal tract (2) including, in downstream order, a stomach (4), a small intestine (5), and a large intestine (6). The small intestine (5) is subdivided into three portions: the duodenum (8), the jejunum (10), and the ileum (12), listed in downstream order. The duodenum (8) is supported by a suspensory muscle (14) known as the ligament of Treitz, and transitions into the jejunum (10) at the duodenojejunal flexure (16). The ileum (12) transitions into the large intestine (6) at the ileocecal junction (17), also known as the ileocecal valve.

Figure 2:
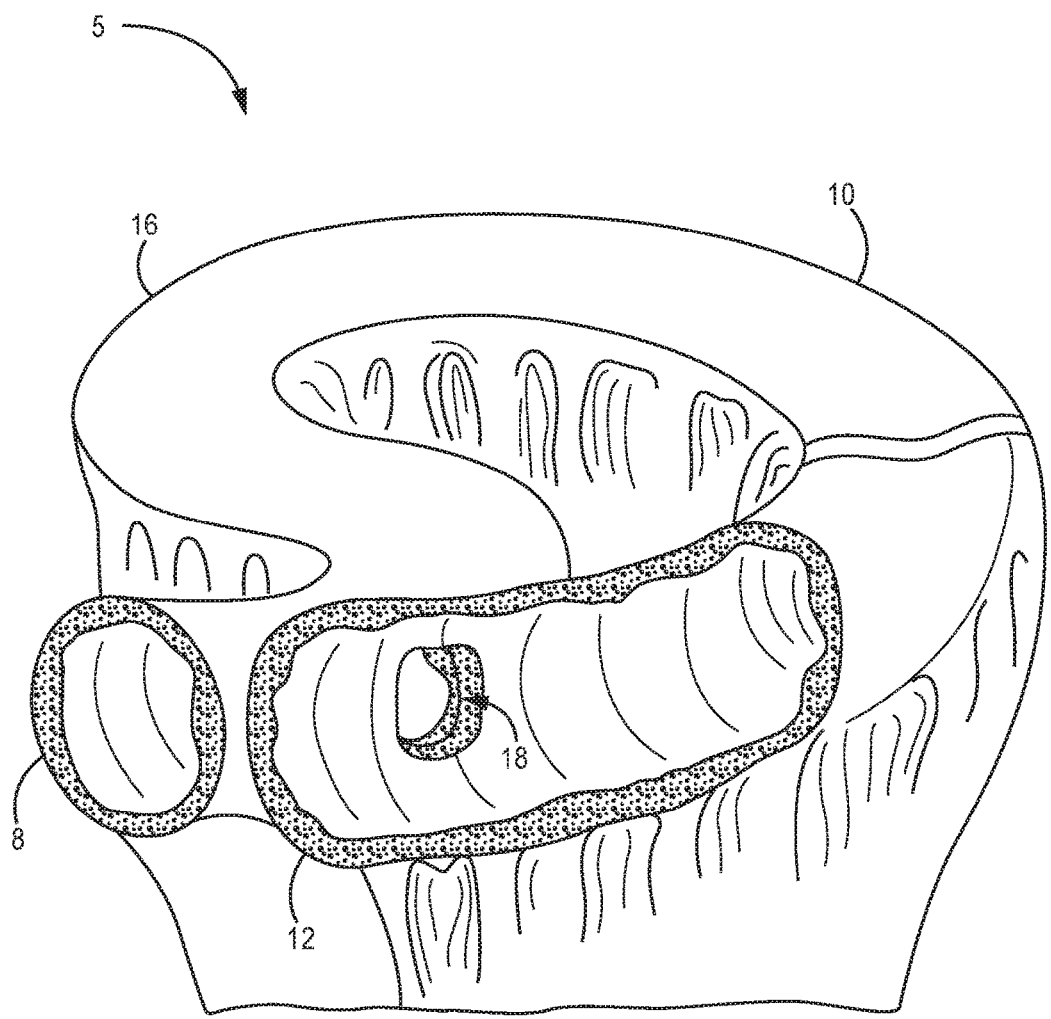
FIG. 2 depicts a partial perspective view of another exemplary side-by-side anastomosis formed in the small intestine.

The gastrointestinal tract (2) is shown including an exemplary anastomosis (18) formed between a proximal portion of the jejunum (10) and the ileum (12). The anastomosis (18) has an inlet side formed through a sidewall of the jejunum (10) at a location adjacent to and downstream of the duodenojejunal flexure (16) and the ligament of Treitz (14). The anastomosis (18) additionally has an outlet side formed through a sidewall of the ileum (12). It will be appreciated that the anastomosis (18) may be positioned at various other suitable locations along the gastrointestinal tract (2). For example, as shown in FIG. 2, the anastomosis (18) may be formed between the duodenum (8) and the ileum (12). Additional exemplary locations of the anastomosis (18) are described in U.S. patent application Ser. No. 15/298,816, entitled "Methods for Partial Diversion of the Intestinal Tract," filed Oct. 20, 2016, published as U.S. Pub. No. 2017/0035425 on Feb. 2, 2017, the disclosure of which is hereby incorporated by referenced herein. It will be further appreciated that the anastomosis (18) may be located elsewhere within a patient's body, other than within the gastrointestinal tract (2). In that regard, it will be understood that the exemplary tissue compression devices shown and described herein may be employed to create anastomoses in various other bodily organs having an internal lumen, and thus are not limited to use in a patient's gastrointestinal tract (2).

Still referring to FIG. 1, the exemplary anastomosis (18) shown provides a pathway for direct fluid communication between the proximal portion of the patient's jejunum (10) and the ileum (12), thereby bypassing a majority of the jejunum (10), located downstream. Consequently, chyme exiting the stomach (4) may flow directly through the duodenum (8), then through the proximal portion of the jejunum (10) and directly into the ileum (12), via the anastomosis (18), without passing through the downstream portion of the jejunum (10). In some instances, a first portion of the chyme exiting the stomach (4) may flow directly from the proximal portion of the jejunum (10) to the ileum (12), via the anastomosis (18). Simultaneously, a second portion of the chyme may pass the anastomosis (18) and flow through the downstream portion of the jejunum (10), rejoining with the first portion of chyme in the ileum (12) before passing into the large intestine (6). Accordingly, the anastomosis (18) may provide a complete diversion or a partial diversion of chyme passing through the jejunum (10).

Forming a side-by-side anastomosis (18) between two portions of the gastrointestinal tract (2), positioned adjacent to one another, may be achieved using a compression device having first and second device portions that clamp intestinal tissue therebetween, as described above. In some procedures, the device portions may be introduced into the intestinal lumen via two or more enterotomies formed in the intestinal sidewalls at respective upstream and downstream locations. In other procedures, the device portions may be introduced into the intestinal lumen endoscopically, using two or more endoscopes inserted through naturally occurring bodily orifices and directed into the intestinal lumen from opposing directions. The exemplary tissue compression devices disclosed herein may be positioned within a patient using either of these methods, for example.

II. Exemplary Anastomosis Tissue Compression Device Having Latching Mechanism

As will be described in greater detail below, the first and second portions of the tissue compression devices disclosed herein may include magnetic members that draw the device portions together. The device portions, when drawn together magnetically, compress tissue positioned therebetween with a clamping force sufficient to cause ischemia and eventual necrosis of the tissue. Once necrosis occurs, the device falls away to reveal an anastomosis, and the device is then passed through the gastrointestinal tract. As will be described, the exemplary tissue compression devices disclosed herein may further include mechanical latching mechanisms that prevent unintended decoupling of the device portions during an anastomosis procedure and after the device portions are freed from the anastomosis site, thereby reinforcing the magnetic coupling provided by the magnetic members.

A. Structural Features of Exemplary Tissue Compression Device

Figure 3:
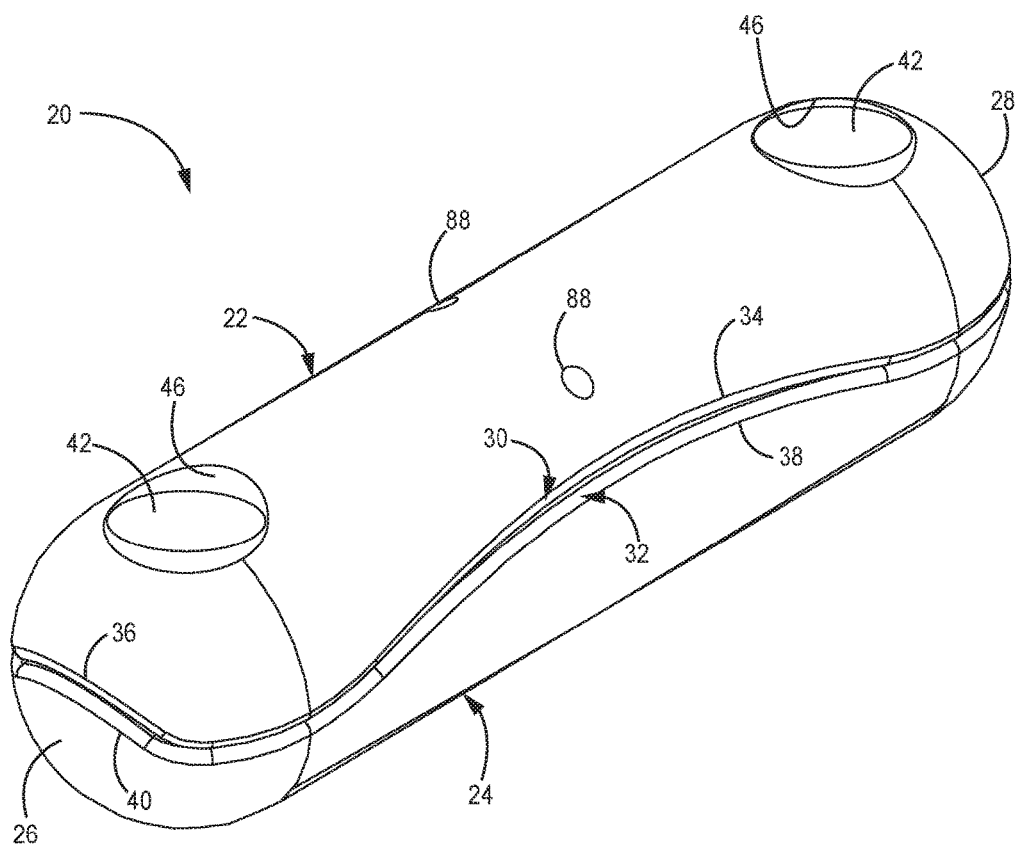
FIG. 3 depicts a perspective view of an exemplary tissue compression device for forming an anastomosis.

FIGS. 3-4B show an exemplary tissue compression device (20) for forming an anastomosis, such as a side-by-side anastomosis, in an assembled configuration. The tissue compression device (20) includes a first device half (22) and a second device half (24) that mate together to define an elongate device body that extends along a longitudinal device axis between a convexly rounded first end (26) and a convexly rounded second end (28). The device (20) may be formed with a length that is greater than its width so as to present a pill-like shape. Each device half (22, 24) may be formed as a unitary structure having non-articulating features, as described below.

As best shown in FIGS. 4A and 4B, the tissue compression device (20) may be formed with a transverse cross-section having a rounded shape to provide the device (20) with a rounded and smooth outer periphery that is atraumatic to patient tissue. As best shown in FIG. 4B, the exemplary device (20) is formed with a generally circular shaped cross-section. Additionally, as shown in FIG. 4A, the circular cross-section may be uniform in diameter along a medial portion of the device (20) extending between its first and second rounded ends (26, 28). In alternative variations, the device (20) may be formed with a transverse cross-section of various other shapes, such as various rounded shapes, and the cross-section may be uniform or non-uniform (e.g., tapered) along a length of the device (20).

Figure 5:
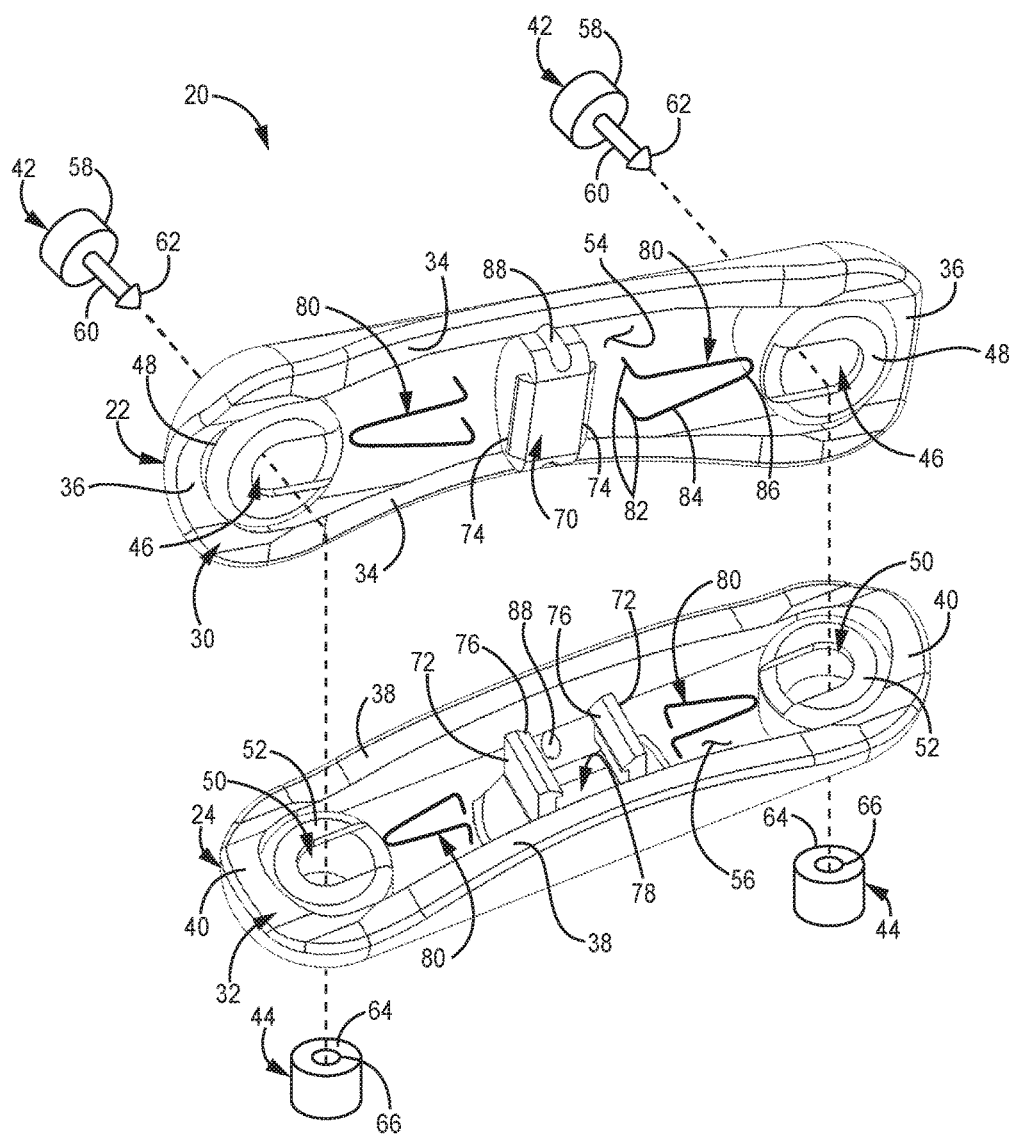
FIG. 5 depicts a disassembled perspective view of the tissue compression device of FIG. 3.

FIG. 5 shows the device (20) in a disassembled configuration to reveal additional structural features. For illustrative purposes only, the first device half (22) is shown in an upper position and the second device half (24) is shown in a lower position. In that regard, it will be appreciated that relative positional terms including "upper," "lower" and similar terms as may be used herein are illustrative only and are not limiting of the features to which they refer nor of the various orientations in which the device (20) may be employed.

As best shown in FIGS. 4A-5, the first device half (22) includes a first mating surface (30) that extends continuously about a perimeter of the mating side of the first device half (22). Similarly, the second device half (24) includes a second mating surface (32) that extends continuously about a perimeter of the mating side of the second device half (24). The first mating surface (30) may be formed with a first contour and the second mating surface (32) may be formed with a second contour that complements the first contour. More specifically, the first mating surface (30) may be formed with elongate concave side portions (34) extending generally parallel to the device axis, and with concave end portions (36) extending generally transverse to the device axis. The second mating surface (32) may be formed with elongate convex side portions (38) extending generally parallel to the device axis, and with convex end portions (40) extending generally transverse to the device axis. As best shown by a comparison of FIGS. 4A and 4B, the side portions (34, 38) of the first and second mating surfaces (30, 32) may be formed with a first radius of curvature, and the end portions (36, 40) may be formed with a second, differing radius of curvature. The mating surfaces (30, 32) may exhibit additional geometric features as disclosed in U.S. patent application Ser. No. 15/419,132, entitled "Elongated Tissue Compression Device System with Smooth Outer Contour and Orthogonal Curved Aligning Surfaces," filed on Jan. 30, 2017, now published as U.S. Pub. No. 2018/0214149 on Aug. 2, 2018, the disclosure of which is hereby incorporated by reference herein. In other versions, though not shown, the mating surfaces (30, 32) may be formed with various alternative complementary contours, or with fully or partially planar configurations, for example.

Still referring to FIG. 5, the first device half (22) houses a pair of first magnetic members (42) and the second device half (24) houses a pair of second magnetic members (44). The first and second magnetic members (42, 44) are oriented with opposing magnetic polarizations such that magnetic members (42, 44) magnetically attract one another to thereby draw the first and second device halves (22, 24) together in confronting relationship and compress tissue therebetween, as described in greater detail below. While the magnetic members (42, 44) are shown herein in the form of permanent magnets, in alternative versions the magnetic members (42, 44) may be in the form of electromagnets, such as those disclosed in U.S. patent application Ser. No. 15/419,102, entitled "Battery Powered Electromagnetic Tissue Compression Device," filed Jan. 30, 2017, published as U.S. Pub. No. 2018/0214151 on Aug. 2, 2018, the disclosure of which is hereby incorporated by reference herein.

Figure 8A:
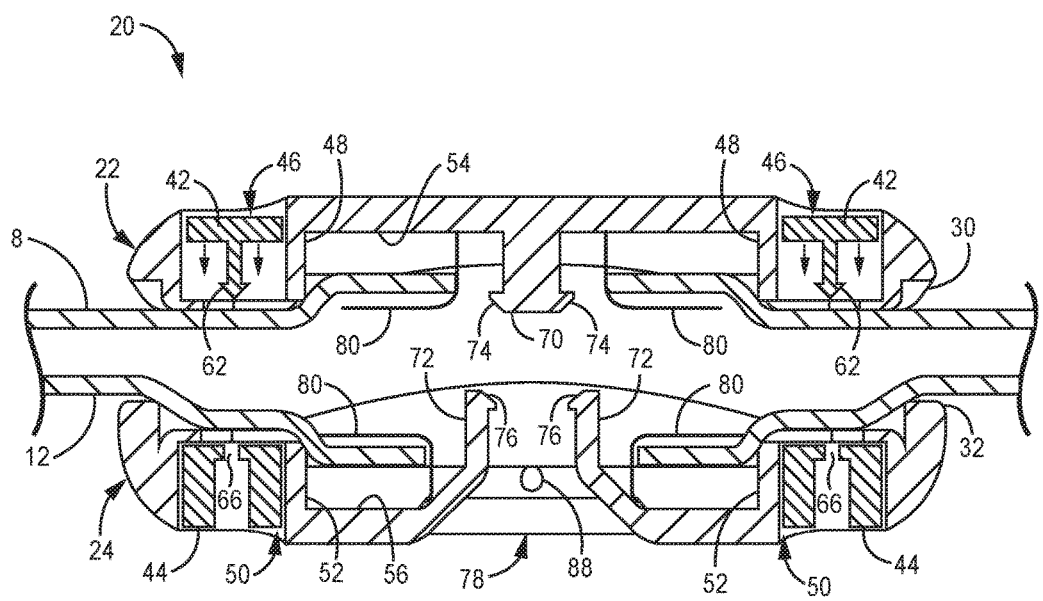
FIG. 8A depicts a side cross-sectional view of the tissue compression device of FIG. 3, shown engaged with sidewalls of the duodenum and ileum, respectively, after having been positioned using the exemplary procedure of FIGS. 6A-6D, with latching mechanisms of the device shown in unlatched states.
Figure 8B:
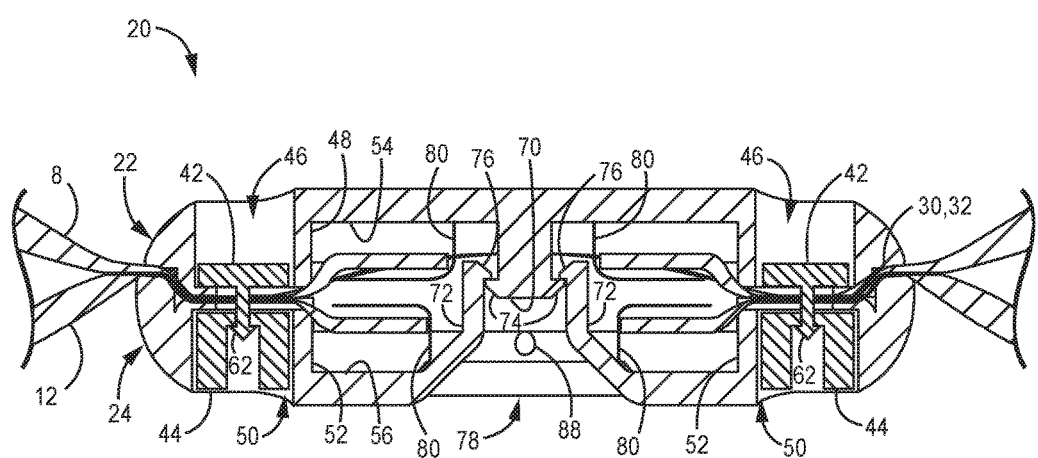
FIG. 8B depicts a side cross-sectional view of the tissue compression device of FIG. 3 in the duodenum and ileum of FIG. 8A, showing the first and second device halves being drawn together magnetically and compressing sidewalls of the duodenum and the ileum therebetween to induce necrosis of the tissue, with the latching mechanisms shown in latched states.

Each of the first magnetic members (42) is received within a socket (46) of a magnet retaining structure (48) arranged at a respective end of the first device half (22). Similarly, each of the second magnetic members (44) is received within a socket (50) of a magnet retaining structure (52) arranged at a respective end of the second device half (24). Each socket (46, 50) extends generally transversely to the device axis, and opens at a first end to the rounded outer periphery of the respective device half (22, 24), and opens at a second end to the mating side of the device half (22, 24). The first device half (22) includes a first recessed base wall (54) from which the magnet retaining structures (48) project in a direction toward the device axis. Similarly, the second device half (24) includes a second recessed base wall (56) from which the magnet retaining structures (52) project in a direction toward the device axis. As shown in FIG. 8B, the device halves (22, 24) mate together to define a closed interior cavity bounded by the recessed base walls (54, 56) and the magnet retaining structures (48, 52).

Each of the first magnetic members (42) of the first device half (22) may include a disc-like base (58) and a shaft (60) extending away from the base (58) and terminating at a barbed tip (62). Each of the second magnetic members (44) may be generally cylindrical with an end wall (64) and a bore (66) extending through the end wall (64). The bore (66) may be sized and shaped to receive therethrough the barbed tip (62) of the corresponding first magnetic member (42), with slight elastic deflection of the barbed tip (62) and/or the end wall (64). In that regard, at least the barbed tip (62) and/or end wall (64) may be formed of a suitably resilient material configured to elastically deflect to allow for a snap-fit engagement of the first magnetic member (42) with the second magnetic member (44). Additionally, the sockets (46) of the first magnet retaining structures (48) may be sized to receive the first magnetic members (42) such that the magnetic members (42, 44) are slidable axially within the sockets (46). By comparison, the second magnetic members (44) may be secured axially within their respective sockets (50), such as by a bond or a compression fit, for example. Engagement of the first magnetic members (42) with the second magnetic members (44) is described in greater detail below in connection with FIGS. 8A and 8B.

The tissue compression device (20) shown in FIG. 5 further includes a latching mechanism that is configured to mechanically couple the first device half (22) with the second device half (24) when the devices halves (22, 24) are drawn together by the magnetic members (42, 44). In that regard, the latching mechanism prevents against unintentional decoupling of the device halves (22, 24) during use, and serves to reinforce the magnetic coupling generated by the magnetic members (42, 44). The latching mechanism includes a first latching member in the form of a latching head (70) fixedly coupled to the first device half (22), and which projects from the first recessed base wall (54) in a direction toward the device axis. The latching mechanism further includes a second latching member in the form of a pair of latching arms (72) fixedly coupled to the second device half (24) and projecting from the second recessed base wall (56) in a direction toward the device axis. The latching head (70) and latching arms (72) may be formed integrally with the first and second device halves (22, 24), respectively. Additionally, the latching head (70) and latching arms (72) are arranged inwardly of the outer periphery of the device (20), and thus are shielded from exposure to external influence during use and enable the device (20) to maintain a smooth outer periphery.

In the example shown, the first latching member (70) is configured as a male component and the second latching member (72) is configured as a female component adapted to receive the first latching member (70) with a snap-fit locking engagement. It will be appreciated that a reverse configuration may be provided in alternative versions. Additionally, while the tissue compression device (20) is shown having a single male latching member and a single female latching member, alternative versions of the device (20) may include multiple male-female pairs of latching members.

The latching head (70) includes a pair of chamfered shoulders (74) extending laterally outwardly from opposing sides of a distal end of the head (70). The latching arms (72), extending from the second device half (24), confront one another and are spaced apart with a width suitable to accommodate the latching head (70) between the latching arms (72) with a snap-fit engagement. Each latching arm (72) includes a chamfered finger (76) that projects laterally inwardly in a direction toward the opposing latching arm (72). As shown in FIGS. 8A and 8B, as the magnetic members (42, 44) draw the first and second device halves (22, 24) together, the latching head (70) is received between the latching arms (72), and the chamfered shoulders (74) of the latching head (70) engage the chamfered fingers (76) of the latching arms (72). As the device halves (22, 24) continue to advance toward one another, the latching head (70) is forced into further engagement with the latching arms (72). As a result, the latching arms (72) resiliently deflect outwardly to enable the chamfered shoulders (74) to slip past the chamfered fingers (76), at which point the latching arms (72) then spring back toward their relaxed state to establish a snap-fit-engagement with the latching head (70), secured by the shoulders (74) and the fingers (76).

The latching mechanism of the tissue compression device (20) may be releasable. As shown best in FIGS. 5 and 8A-8B, the second device half (24) may include an opening (78) formed between inwardly angled base portions of the latching arms (72). If a medical practitioner chooses to decouple the device halves (22, 24) after they have been coupled via engagement of the latching members (70, 72), a tool (not shown) may be inserted through the opening (78) and levered against one or both of the latching arms (72) to deflect them outwardly and thereby disengage the chamfered fingers (76) from the chamfered shoulders (74). Upon disengagement, the device halves (22, 24) may be more easily separated from one another. Various suitable forms that a latching arm (72) disengagement tool may take will be apparent to those of ordinary skill in the art in view of the teachings herein.

Still referring to FIG. 5, each of the first and second device halves (22, 24) may further include a pair of resilient retaining clips (80). Each retaining clip (80) includes a pair of legs (82) that couple to and project from the respective recessed base wall (54, 56) in a direction toward the device axis, and a body (84) that bends away from legs (82) in a direction generally parallel to the device axis. The body (84) terminates at a looped tip (86) oriented toward a respective magnet retaining structure (48, 52). The retaining clips (80) may be formed of any suitable resilient material, such as nitinol for example, and may include additional features and functionality of resilient members (130) disclosed in U.S. patent application Ser. No. 15/298,816, published as Pub. No. 2017/0035425 on Feb. 9, 2017, incorporated by reference above. In some versions, retaining clips (80) comprise a ferrous material. In some such versions, retaining clips (80) experience some degree of magnetic attraction from magnetic members (42, 44). In some other versions, the retaining clips (80) are completely non-ferrous, such that magnetic members (42, 44) do not magnetically attract retaining clips (80). In the present example, each clip (80) is resiliently flexible at bends between its legs (82) and its body (84) for flexing between a relaxed state, shown in FIG. 5, and one or more flexed states, shown in FIGS. 6A and 6B. As described below, the retaining clips (80) are operable to retain the respective device half (22, 24) in place within an enterotomy formed in a sidewall of an organ during an anastomosis procedure.

In addition to, or alternatively in place of, the retaining clips (80), each device half (22, 24) may include one or more pairs of suture bores (88) for suturing the device half (22, 24) to an organ in which the device half (22, 24) is inserted. As shown best in FIGS. 3-5, the suture bores (88) may extend through an outer periphery of each device half (22, 24) and transversely to the device axis at locations spanning the lateral sides of the latching head (70) and the latching arms (72). The suture bores (88) may be employed with suture materials and methods as disclosed in U.S. patent application Ser. No. 15/419,151, entitled "Tissue Compression Device with Features to Contain Needles and Suture During Packaging and Placement in Body," filed on Jan. 30, 2017, published as U.S. Pub. No. 2018/0214152 on Aug. 2, 2018, the disclosure of which is hereby incorporated by reference herein.

B. Exemplary Procedures for Forming an Anastomosis Using Exemplary Tissue Compression Device Having Latching Mechanism Referring to FIGS. 6A-6F, an exemplary procedure will now be described for deploying a device half (22, 24) of the tissue compression device (20), using an instrument (90), within the gastrointestinal tract (2) of a patient at the site of an anastomosis to be formed. While the deployment steps illustrated in FIGS. 6A-6D are shown in connection with the first device half (22), it will be understood that similar steps may be taken to deploy the second device half (24).

Figure 6A:
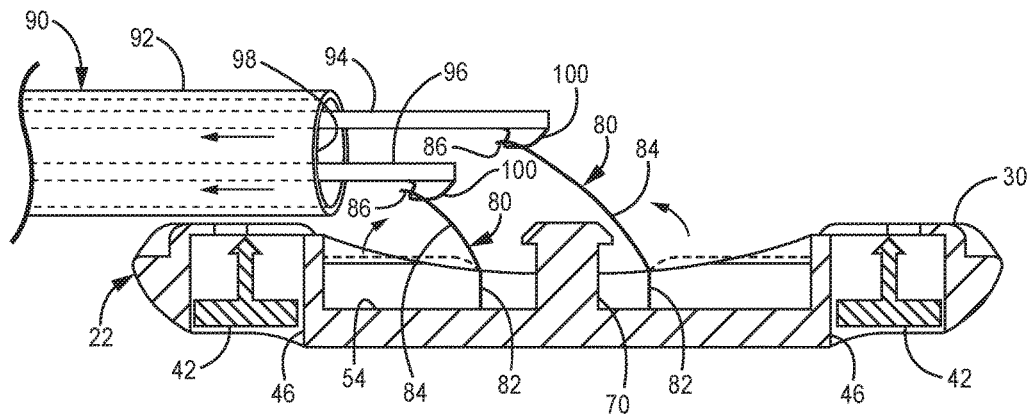
FIG. 6A depicts a side cross-sectional view of a first device half of the tissue compression device of FIG. 3, shown with retaining clips thereof engaged with the distal end of an exemplary instrument operable to deploy the device halves within a patient, with inner members of the instrument shown in extended positions.
Figure 6B:
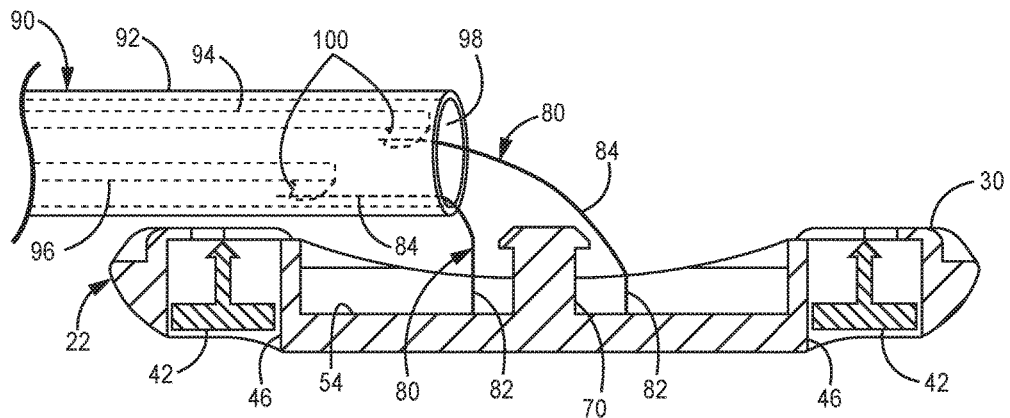
FIG. 6B depicts a side cross-sectional view of the first device half and instrument of FIG. 6A, showing the inner members of the instrument in retracted positions.

As shown in FIGS. 6A and 6B, the exemplary instrument (90) includes an outer sheath (92) and first and second elongate inner members (94, 96) spaced radially from one another. A distal end of the outer sheath (92) includes an opening (98) through which distal ends of the inner members (94, 96) slidably extend and retract. The inner members (94, 96) are slidably disposed within the outer sheath (92), and each inner member (94, 96) is translatable between an extended position, shown in FIG. 6A, and a retracted position, shown in FIG. 6B. The distal end of each inner member (94, 96) includes a hook element (100) configured to engage and releasably retain the looped tip (86) of a retaining clip (80). The hook element (100) may be rounded at a leading edge so as to minimize undesirable trauma to patient tissue during a placement procedure.

To load the device half (22) onto the instrument (90), as shown in FIG. 6A, the inner members (94, 96) are first extended. The hook element (100) of the first inner member (94) is engaged with the looped tip (86) of a first one of the retaining clips (80), and the hook element (100) of the second inner member (96) is engaged with the looped tip (86) of a second one of the retaining clips (80). As shown in FIG. 6A, the hook element (100) of the first inner member (94) may be extended distally beyond the hook element (100) of the second inner member (96) to reach its respective retaining clip (80). Once the looped tips (86) have been retained on the hook elements (100), the inner members (94, 96) are retracted into the outer sheath (92). As described above, the retaining clips (80) are configured to resiliently flex between relaxed and flexed positions, without permanent deformation.

Figure 6C:
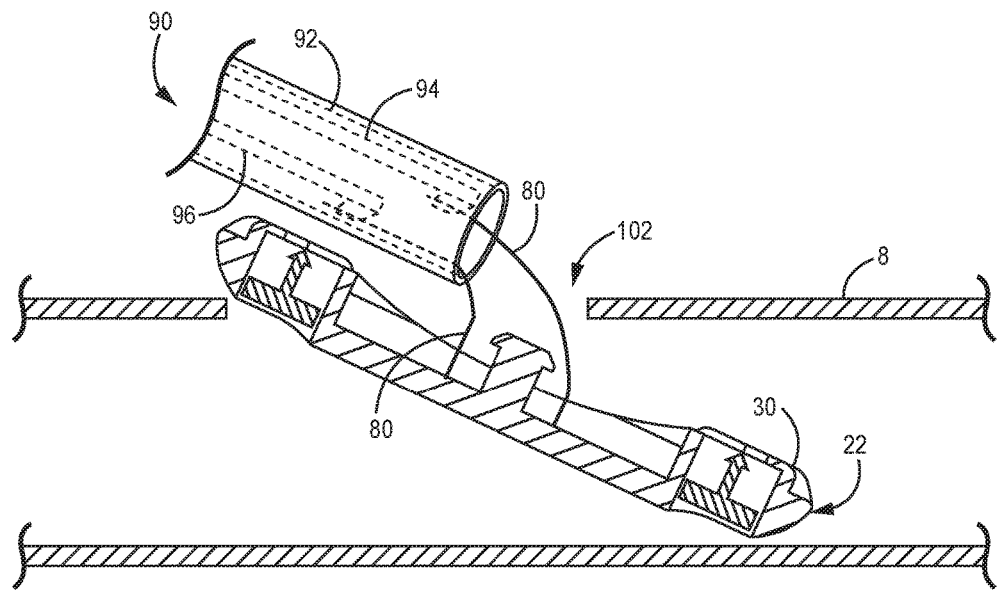
FIG. 6C depicts a side cross-sectional view of a patient's digestive system during deployment of the tissue compression device of FIG. 3 for an anastomosis procedure, showing the first device half being inserted through an opening formed in the patient's duodenum with the instrument of FIG. 6A.
Figure 6D:
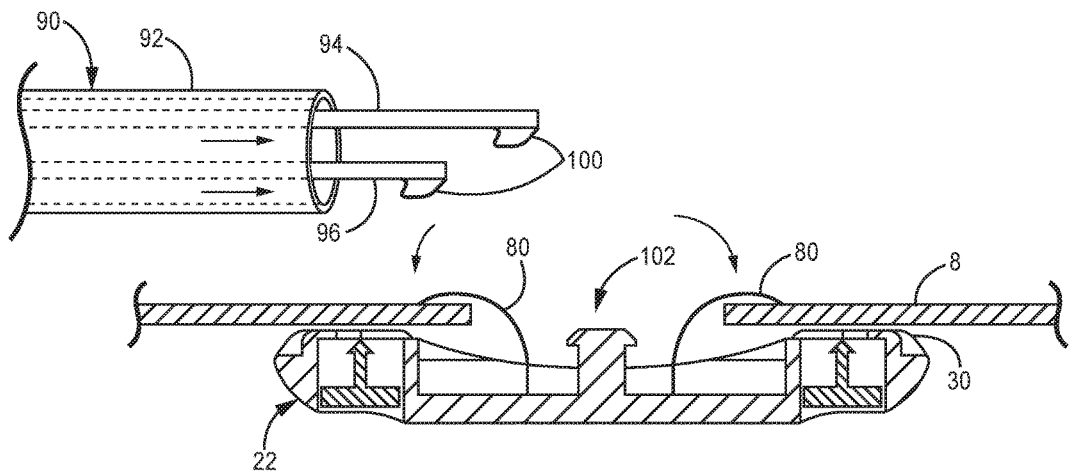
FIG. 6D depicts a cross-sectional view of the patient's digestive system of FIG. 6C later during deployment of the tissue compression device of FIG. 3 for an anastomosis procedure, showing the inner members of the instrument moved to the extended position to release the retaining clips of the device half into a deployed state for engaging the sidewall of the patient's duodenum.

As shown in FIG. 6C, the loaded device half (22) is inserted by the instrument (90) through an enterotomy (102) formed in the sidewall of an organ in which an anastomosis is to be created. In the exemplary illustrated version, the organ is shown in the form of the duodenum (8) of a patient's small intestine (5). Alternatively, device half (22) may be inserted in any other suitable portion of the patient's gastrointestinal tract (2). Though not shown, a proximal end of the instrument (90) is manipulated by a surgeon to properly locate the device half (22) within the enterotomy (102). As shown in FIG. 6D, once the device half (22) has been suitably positioned within the enterotomy (102), the inner members (94, 96) of the instrument (90) are extended through the distal opening (98) into their extended positions so the hook elements (100) disengage the looped tips (86) of the retaining clips (80). Consequently, the retaining clips (80) may spring back to their relaxed states and capture the tissue sidewall (8) against the mating surface (30) of the device half (22). In this manner, the device half (22) is held securely in place relative to the enterotomy (102), and the instrument (90) may be removed from the patient. The same process may then be repeated for deploying the second device half (24) within the patient, for example within a second enterotomy formed in the patient's ileum (12). Again, in other procedures, second device half (24) may be inserted in any other suitable portion of the patient's gastrointestinal tract (2).

Figure 6E:
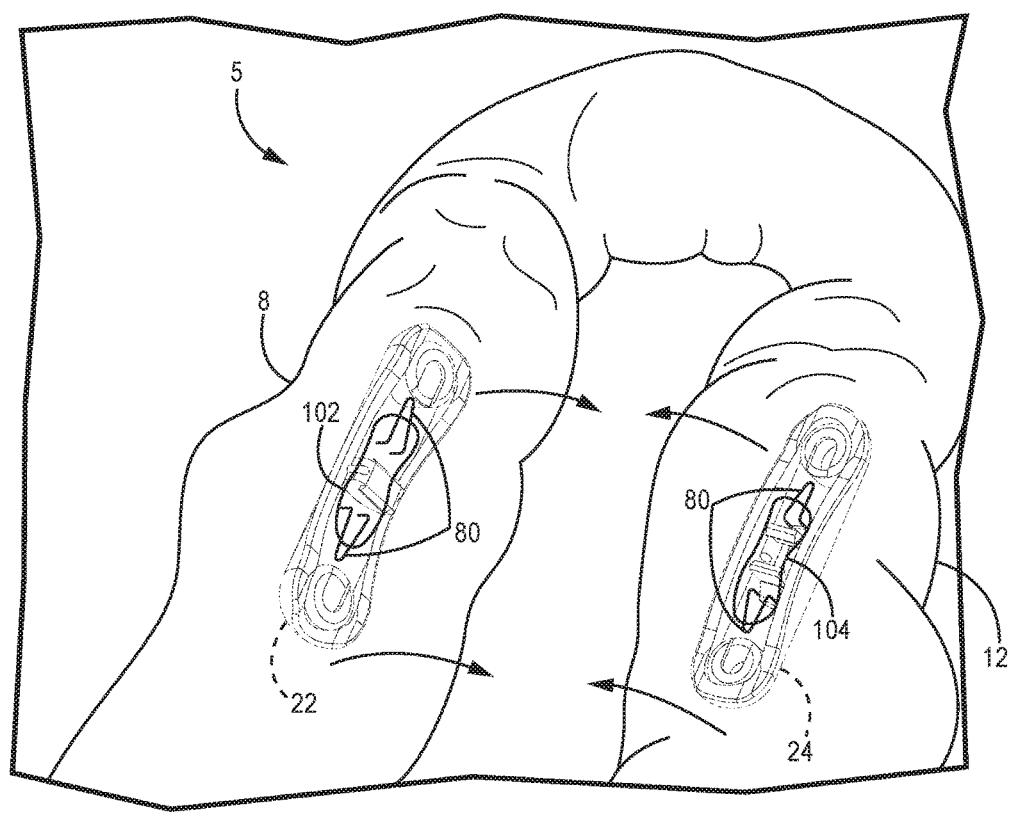
FIG. 6E depicts a perspective view of the patient's digestive system following deployment of the first and second device halves according to the exemplary procedure shown in FIGS. 6A-6D.

FIG. 6E shows the first device half (22) positioned and centered within a first enterotomy (102) formed in the patient's duodenum (8), and the second device half (24) positioned and centered within a second enterotomy (104) formed in an adjacent portion of the patient's ileum (12). The instrument (90) has been removed from the patient and the retaining clips (80) maintain the device halves (22, 24) in position. As indicated by the directional arrows in FIG. 6E, the adjacent portions of the duodenum (8) and the ileum (12), in which the device halves (22, 24) have been deployed, may be repositioned as necessary to arrange the first and second enterotomies (102, 104) in confronting relation.

Figure 6F:
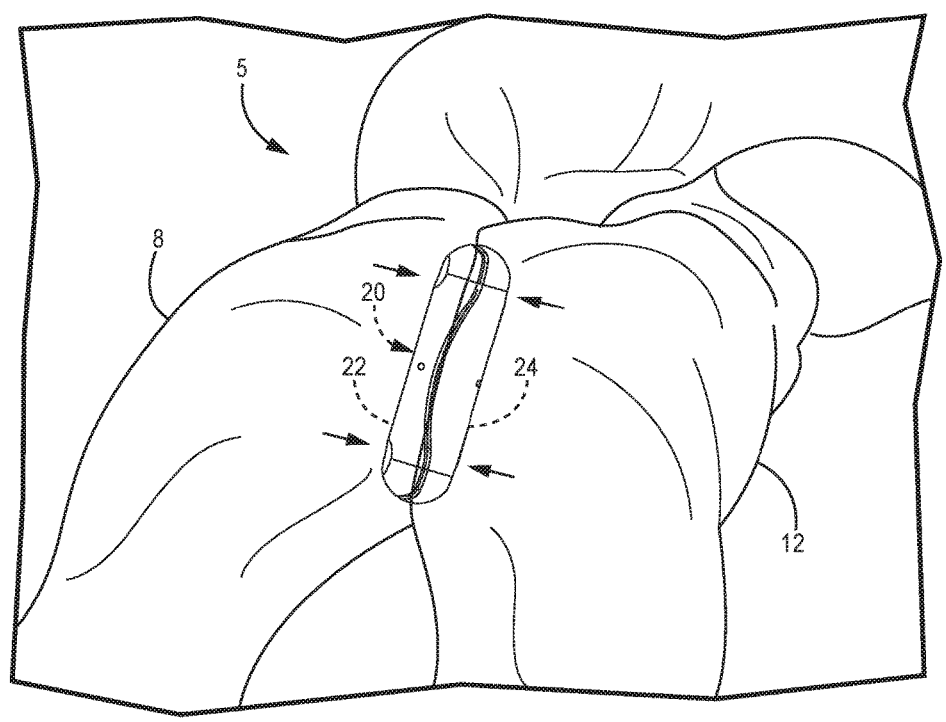
FIG. 6F depicts a perspective view of the patient's digestive system, showing magnetic attraction of the first and second device halves following deployment according to the exemplary procedure of FIGS. 6A-6D.

As shown in FIG. 6F, once the device halves (22, 24) are brought within proximate range of each another, the first and second magnetic members (42, 44) of the device halves (22, 24) (see FIG. 5) mutually attract one another and draw the two device halves (22, 24) together. As described in greater detail below in connection with FIGS. 8A-8C, the device halves (22, 24) thereby compress the sidewalls of the duodenum (8) and the ileum (12) between their mating surfaces (30, 32), and cause the formation of an anastomosis.

Figure 7A:
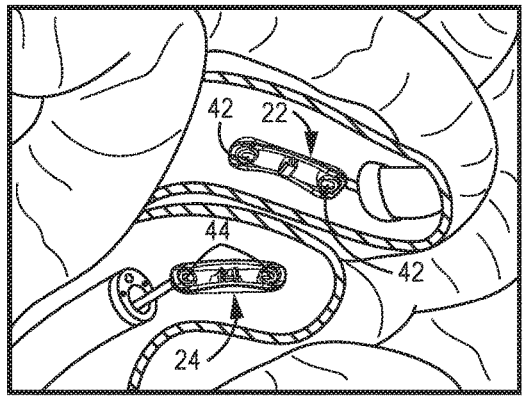
FIG. 7A depicts a partial perspective view of another exemplary procedure for deploying the tissue compression device of FIG. 3 within the small intestine of a patient, using endoscopes.
Figure 7B:
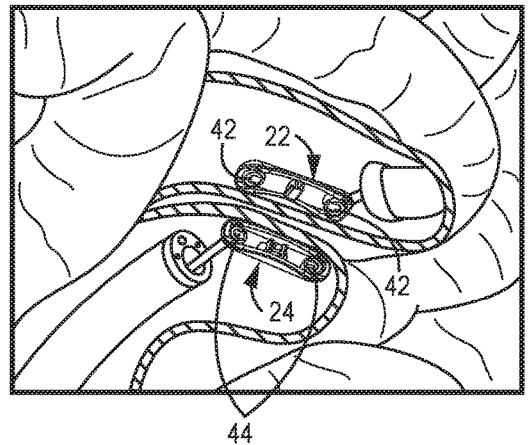
FIG. 7B depicts a partial perspective view of the procedure of FIG. 7A, showing the first and second device halves being aligned with one another within their respective adjacent portions of the patient's small intestine, using the endoscopes.
Figure 7C:
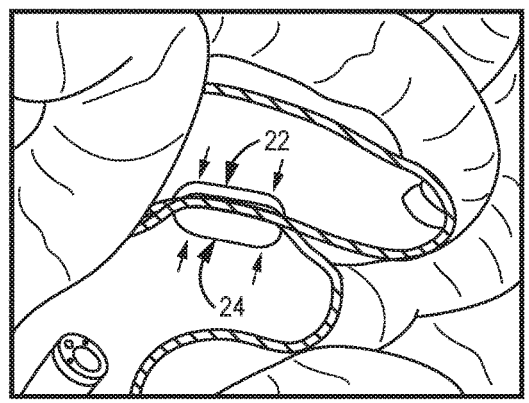
FIG. 7C depicts a partial perspective view of the procedure of FIG. 7A, showing the first and second device halves disengaged from the endoscopes and being drawn together magnetically to compress tissue therebetween for forming an anastomosis.

As described above, the exemplary device deployment procedure shown in FIGS. 6A-6F includes the formation of enterotomies (102, 104) in the patient's gastrointestinal tract (2). In some instances, it may be desirable to avoid formation of such enterotomies (102, 104). FIGS. 7A-7C show an exemplary alternative device deployment procedure in which the device halves (22, 24) are deployed within the patient's gastrointestinal tract (2) using endoscopes (106, 108), and without forming enterotomies in the tract (2). In this version, the retaining clips (80) are not used and may be omitted from the tissue compression device (20), if desired.

Referring to FIG. 7A, the first device half (22) is loaded onto a retractable inner member (110) of a first endoscope (106), and the second device half (24) is loaded onto a retractable inner member (110) of a second endoscope (108). The endoscopes (106, 108) may be of any suitable types known in the art. The first endoscope (106) may then be inserted through a first natural body orifice (e.g., mouth) at a first end of the patient's gastrointestinal tract (2), and the second endoscope (108) may be inserted through a second natural body orifice (e.g., rectum) located at a second end of the gastrointestinal tract (2). The distal ends of the endoscopes (106, 108), loaded with the device halves (22, 24), are then routed through the gastrointestinal tract (2), from opposing directions, toward a site at which an anastomosis is to be formed.

Referring to FIG. 7B, the exemplary site for anastomosis formation is shown selected at adjacent portions of the patient's duodenum (8) and ileum (12). Upon reaching the anastomosis site, the endoscopes (106, 108) are manipulated to approximately align the device halves (22, 24) such that their mating surfaces (30, 32) (see FIG. 5) confront one another. As shown in FIG. 7C, upon the device halves (22, 24) being approximately aligned, the magnetic members (42, 44) attract one another through the tissue sidewalls (8, 12) and draw the device halves (22, 24) together, thereby compressing the sidewalls (8, 12) between the device halves (22, 24). The magnetic members (42, 44) hold the device halves (22, 24) securely in place relative to each other and relative to the tissue sidewalls (8, 12). The inner members (110) of the endoscopes (106, 108) may then be detached from the device halves (22, 24) and retracted, and the endoscopes (106, 108) may be removed from the patient by reversing them through the gastrointestinal tract (2).

Figure 8C:
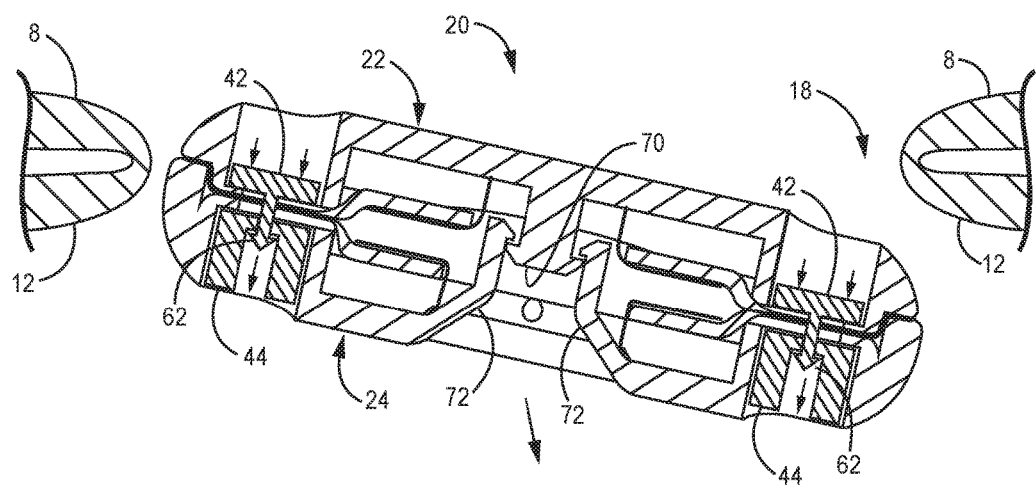
FIG. 8C depicts a side cross-sectional of the tissue compression device of FIG. 3 in the duodenum and ileum of FIG. 8A, showing the compressed tissue in a fully necrosed state, and the device falling away to reveal an anastomosis between the duodenum and ileum.

Referring to FIGS. 8A-8C, formation of an exemplary anastomosis in sidewalls of the patient's duodenum (8) and ileum (12) is shown. The device halves (22, 24) are shown including retaining clips (80), and thus FIGS. 8A-8C may be understood to show the device halves (22, 24) after having been positioned using the exemplary instrument (90) and procedure shown in FIGS. 6A-6D. However, as described above, the device halves (22, 24) may alternatively be positioned using the exemplary endoscopic procedure shown in FIGS. 7A-7C, in which case enterotomies are not formed in the intestinal sidewalls and the retaining clips (80) may be omitted from the device halves (22, 24). It will be appreciated that the device engagement steps described below, and the resulting anastomosis formation, may apply regardless of the technique used to initially position the device halves (22, 24) within the patient.

Starting with FIG. 8A, the first device half (22) is shown supported by its retaining clips (80) within first enterotomy (102) formed in the sidewall of the duodenum (8), and the second device half (24) is shown supported by its retaining clips (80) within the second enterotomy (104) formed in the sidewall of the ileum (12). The duodenum (8) and ileum (12) have been positioned so that the enterotomies (102, 104), and the device halves (22, 24) arranged therein, confront one another, for example as shown in FIGS. 6E and 6F, described above. Such positioning brings the first magnetic members (42) into close enough range with the second magnetic members (44) that the magnetic members (42, 44) begin to attract one another and draw the two device halves (22, 24) together. As described above, the first magnetic members (42) are slidable axially within their respective magnet retaining structures (48). FIG. 8A shows the first magnetic members (42) in a first position in which their barbed tips (62) confront the duodenum sidewall (8) through openings formed at interior ends of the magnet retaining structures (48), seen also in FIG. 5.

As shown in FIG. 8B, magnetic attraction between the first and second magnetic members (42, 44) draws the first and second device halves (22, 24) together. As the device halves (22, 24) draw together, the latching head (70) of the first device half (22) lockingly engages the latching arms (72) of the second device half (24), thereby securely coupling the first device half (22) with the second device half (24). The magnetic drawing together of the device halves (22, 24) also operates to compress the duodenum sidewall (8) and the ileum sidewall (12) between the mating surfaces (30, 32) of the device halves (22, 24). Simultaneously, the first magnetic members (42) are drawn axially within their sockets (46) toward the second magnetic members (44), which causes the barbed tips (62) of the first magnetic members (42) to pierce through the duodenum sidewall (8) and pass into the bores (66) of the second magnetic members (44). As described above, the barbed tips (62) may be sized with a diameter slightly larger than a diameter of the bores (66), and may resiliently deflect to pass through the bores (66) to achieve a snap-fit locking engagement between the first and second magnetic members (42, 44). In this manner, the magnetic members (42, 44) may operate as a secondary latching mechanism in addition to the primary latching mechanism defined by the latching head (70) and the latching arms (72). Similar to the locking engagement between the latching head (70) and latching arms (72), the locking engagement between the first and second magnetic members (42, 44) may be releasable.

Compression of the duodenum sidewall (8) and the ileum sidewall (12) between the device halves (22, 24) induces serosa-to-serosa adhesion between the sidewalls (8, 12), about the outer perimeter of the tissue compression device (20). Additionally, the compressive clamping force exerted by the mating surfaces (30, 32) is sufficient to cause ischemia and eventual necrosis in the clamped tissue (8, 12). With passage of time, such as approximately four days to two weeks, for example, the compressed tissue fully necroses and detaches from the surrounding healthy tissue of the sidewalls (8, 12). As shown in FIG. 8C, detachment of the necrosed tissue from the surrounding healthy tissue releases the tissue compression device (20) into the small intestine (5), and reveals a formed anastomosis (18). The device (20) continues on through the large intestine (6) and is eventually passed by the patient. Advantageously, the smooth outer periphery and low-profile configuration of the device (20) facilitates downstream passage of the device (20) through the gastrointestinal tract (2), including the ileocecal valve (17), for example.

Figure 9:
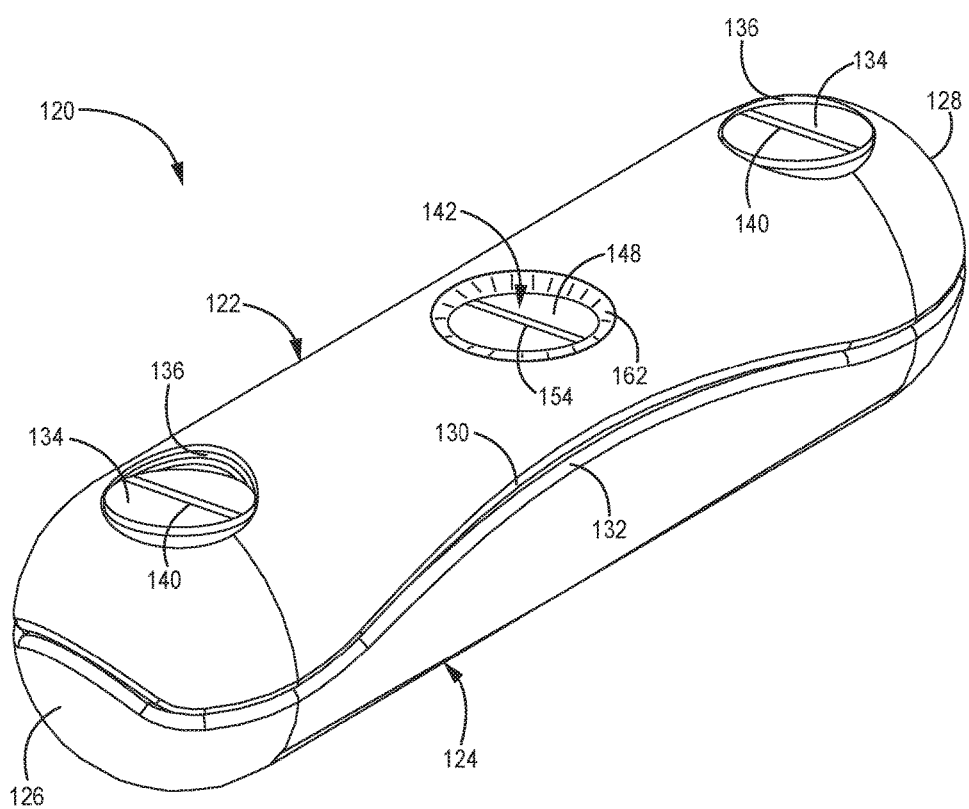
FIG. 9 depicts a perspective view of another exemplary tissue compression device for forming an anastomosis.

C. Exemplary Alternative Anastomosis Tissue Compression Device Having Rotatable Latching Mechanism FIG. 9 shows an exemplary alternative tissue compression device (120) for forming an anastomosis, such as a side-by-side anastomosis, in an assembled configuration. The tissue compression device (120) includes a first device half (122)

and a second device half (124) that mate together to define an elongate device body that extends along a longitudinal device axis between a convexly rounded first end (126) and a convexly rounded second end (128).

Similar to tissue compression device (20) described above, tissue compression device (120) may be formed with a length that is greater than its width so as to present a pill-like shape. Additionally, device (120) may be formed with a transverse cross-section having a rounded shape to provide the device (120) with a rounded and smooth outer periphery that is atraumatic to patient tissue. Further, the device (120) includes first and second mating surfaces (130, 132) similar in geometric arrangement and function to the first and second mating surfaces (30, 32) of device (20). Accordingly, device (120) is similar in geometric configuration to device (20) described above. Unique features of device (120) are described in greater detail below.

Figure 10A:
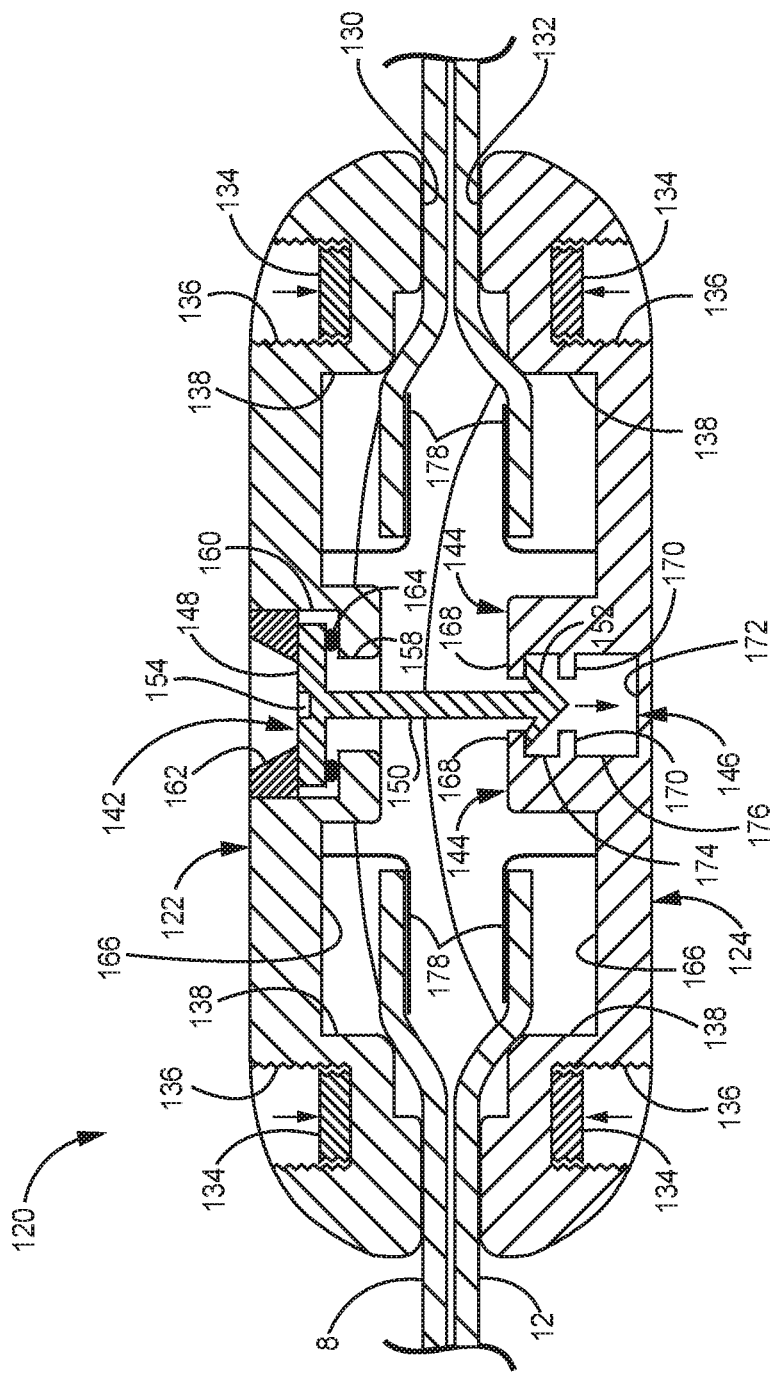
FIG. 10A depicts a side cross-sectional view of the tissue compression device of FIG. 9, with first and second device halves of the device shown engaged with sidewalls of the duodenum and ileum, respectively, after having been positioned using the exemplary anastomosis procedure of FIG. 6A-6D, with the device halves being drawn together magnetically to urge a latching mechanism of the device shown into a first latched state.

Referring to FIGS. 9 and 10A, the first device half (122) of tissue compression device (120) houses a first pair of magnetic members (134), and the second device half (124) houses a second pair of magnetic members (134). Each of the magnetic members (134) is received within a socket (136) of a magnet retaining structure (138) arranged at a respective end of the corresponding device half (122, 124). Each of the magnetic members (134) may be generally disc-like or cylindrical in shape, and may include a threaded outer surface configured to threadedly engage a threaded inner surface of its respective socket (136), as shown in FIG. 10A. Each magnetic member (130) may be rotatably threaded into its respective threaded socket (136) using a tool (not shown) engaged with a tool engagement recess (140) formed in an end surface of the magnetic member (130), as shown in FIG. 9. It will be appreciated that in alternative versions, threading of the magnetic members (134) and the sockets (136) may be omitted, and/or the magnetic members (134) may be fixed within their respective magnet retaining structures (138). Alternatively, the magnetic members (134) may be configured as male and female components similar to the magnetic members (42, 44) of tissue compression device (20), described above.

Figure 10B:
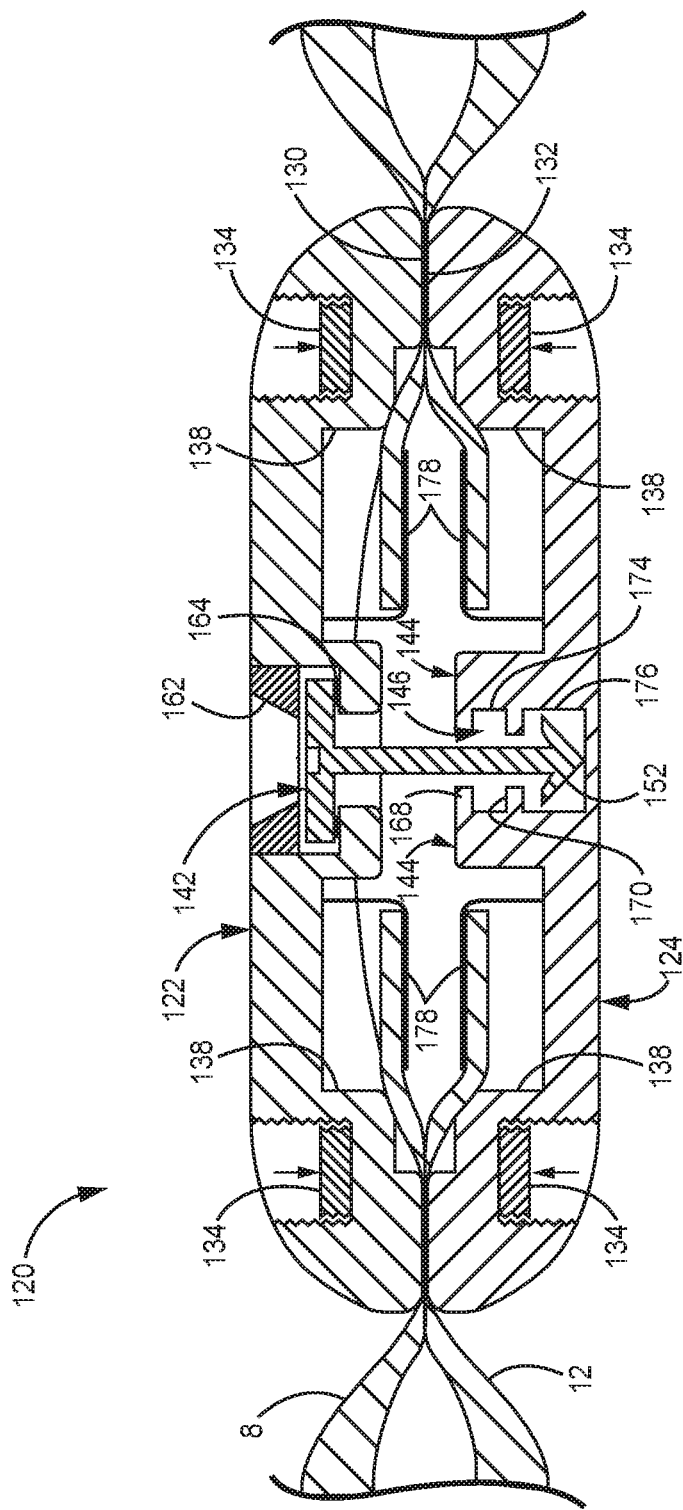
FIG. 10B depicts a side cross-sectional view of the tissue compression device of FIG. 9 in the duodenum and ileum of FIG. 10A, showing the device halves being drawn together further to compress tissue therebetween to induce necrosis of the tissue and urge the latching mechanism into a second latched state.

Referring to FIGS. 10A and 10B, the tissue compression device (120) further includes a latching mechanism having a first latching member in the form of a spike member (142), and a second latching member in the form of a pair of latching arms (144). The spike member (142) is operatively coupled with the first device half (122) and extends transversely toward the device axis. The latching arms (144) extend from the second device half (124) transversely toward the device axis, and define a latching socket (146) therebetween. As described in greater detail below, a distal end of the spike member (142) is received within the latching socket (146) as the device halves (122, 124) are magnetically drawn together, thereby coupling the first device half (122) with the second device half (124). As also described in greater detail below, the spike member (142) is selectively rotatable relative to the device halves (122, 124) to release its distal end from the latching socket (146), and thereby facilitate decoupling of the device halves (122, 124).

Figure 12A:
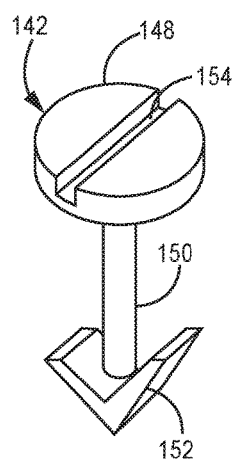
FIG. 12A depicts a perspective view of a spike member of the latching mechanism of the tissue compression device of FIG. 9.
Figure 12B:
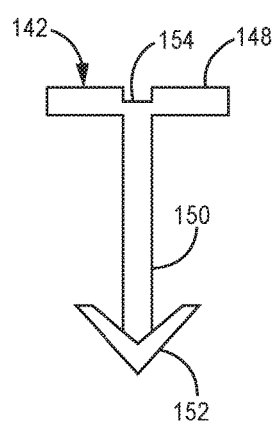
FIG. 12B depicts a front elevational view of the spike member of FIG. 12A.
Figure 12C:
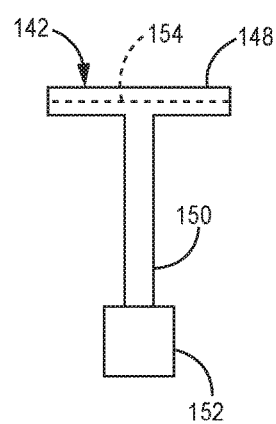
FIG. 12C depicts a side elevational view of the spike member of FIG. 12A.

Referring briefly to FIGS. 12A-12C, the spike member (142) includes a circular head (148), a shaft (150) extending distally from the head (148), and a distal barbed tip (152). An upper end surface of the head (148) may include a tool engagement recess (154) configured to receive a tool (156) (see FIG. 13A) for rotating the spike member (142) relative to the device halves (122, 124). By way of example only, tool engagement recess (154) may be configured to receive a flathead screwdriver head, a Philips screwdriver head, or any other suitable kind of tool head. The barbed tip (152) may be formed as a generally V-shaped extrusion having proximally swept barbs that facilitate advancement of the barbed tip (152) into the latching socket (146), and retention of the barbed tip (152) within the latching socket (146) thereafter, as described below.

Figure 11A:
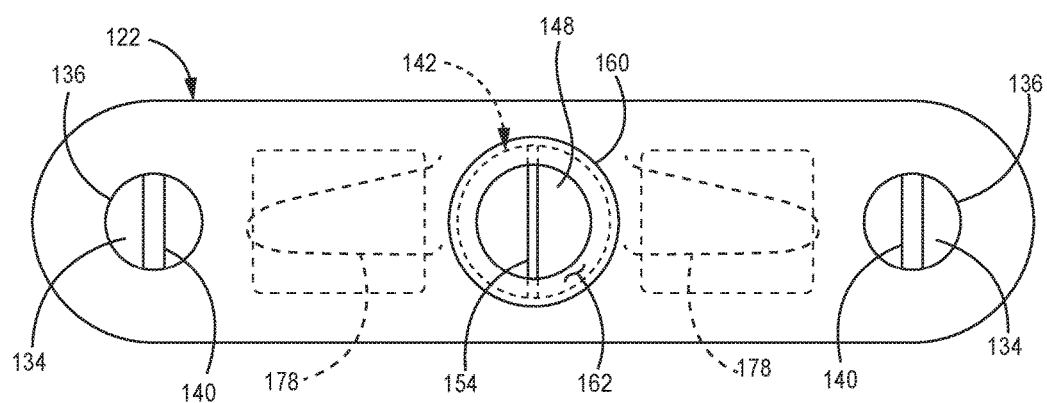
FIG. 11A depicts a top elevational view of the first device half of the tissue compression device of FIG. 9.

Returning to FIGS. 10A and 10B, the first device half (122) includes a through-hole (158) and a counterbore (160) formed centrally between the first and second device ends (126, 128), and which extend coaxially through the first device half (122) in a direction transverse to the device axis. The spike member (142) is mounted to the first device half (122) such that the shaft (150) extends distally through the through-hole (158) and the head (148) is received within the counterbore (160). The head (148) may be retained axially within the counterbore (160) by a retaining ring (162), also shown in FIG. 11A. An annular sealing element (164) may be arranged between the head (148) and a base surface of the counterbore (160) to ensure a sealing engagement of the head (148) with the first device half (122). In some versions, retaining ring (162) and/or sealing element (164) are configured to provide some degree of resistance of head (148), such that retaining ring (162) and/or sealing element (164) will substantially prevent inadvertent rotation of spike member (142) in first device half (122). In such versions, retaining ring (162) and sealing element (164) may nevertheless permit intentional rotation of spike member (142) in first device half (122), such as during a "bail-out" procedure as described below. By way of example only, retaining ring (162) and/or sealing element (164) may provide rotational resistance to head (148) through friction, detenting features, and/or using any other suitable configurations or techniques.

Figure 11B:
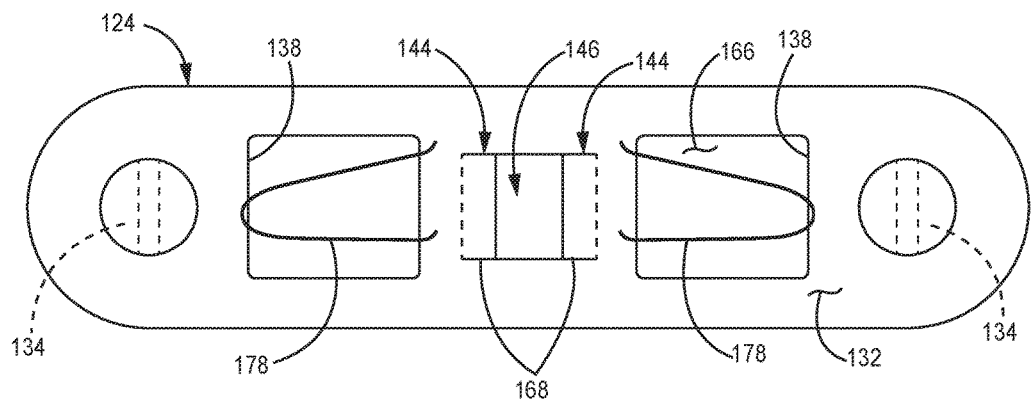
FIG. 11B depicts a top elevational view of the second device half of the tissue compression device of FIG. 9.

The latching arms (144) extend from a recessed base wall (166) of the second device half (124) in a direction toward the device axis, and are spaced apart from one another along the device axis to thereby define the latching socket (146) therebetween. The latching arms (144) may include a confronting pair of first latching fingers (168) arranged at an entrance end of the latching socket (146) (also shown in FIG. 11B), and a confronting pair of second latching fingers (170) arranged toward a base surface (172) of the latching socket (146) in a direction away from the device axis. A first latching chamber (174) is defined between the first fingers (168) and the second fingers (170), and a second latching chamber (176) is defined between the second fingers (170) and the base surface (172).

As shown in FIG. 10A, the device halves (122, 124) may further include retaining clips (178) that are similar in structure and function to the retaining clips (80) described above in connection with tissue compression device (20). Accordingly, the device halves (122, 124) may be positioned within a patient using the instrument (90) and the deployment procedure described above in connection with FIGS. 6A-6D. Alternatively, the retaining clips (178) may be omitted from the device halves (122, 124), and the device halves (122, 124) may be positioned within a patient endoscopically using the procedure described above in connection with FIGS. 7A-7C.

Upon being positioned within a patient at the site of an anastomosis to be formed, such as adjacent portions of the duodenum (8) and the ileum (12), the magnetic members (134) align the first device half (122) with the second device half (124) in a confronting relationship, and draw the device halves (122, 124) together. As the device halves (122, 124) are magnetically drawn together to compress the ileum and duodenum sidewalls (8, 12), the barbed tip (152) of the spike member (142) is received between the latching arms (144)

into the first latching chamber (174) of the latching socket (146), as shown in FIG. 10A. The barbed tip (152) may be formed with a width slightly larger than a corresponding spacing between the first latching fingers (168), such that the barbed tip (152) must resiliently deflect against the first fingers (168) as the barbed tip (152) passes into the first chamber (174). In this manner, the barbed tip (152) lockingly engages the latching arms (144) with a snap-fit engagement. The proximally swept configuration of the barbed tip (152) hinders the tip (152) from flexing so as to recede proximally from the first chamber (174) unintentionally during use.

Referring to FIG. 10B, as the tissue sidewalls (8, 12) necrose and reduce in thickness under compression, the device halves (122, 124) are magnetically drawn further together, forcing the barbed tip (152) of the spike member (142) past the second latching fingers (170) and into the second latching chamber (176) of the latching socket (146). Similar to the relationship described above with the first latching fingers (168), the barbed tip (152) may resiliently deflect against the second latching fingers (170) as the tip (152) advances into the second chamber (176), establishing a snap-fit engagement. Additionally, the proximally swept configuration of the barbed tip (152) hinders the tip (152) from flexing so as to recede proximally from the second chamber (176) unintentionally.

As described above, the spike member (142) and the latching arms (144) are configured to provide multiple, progressive latched states between the device halves (122, 124), thereby accommodating a decreasing thickness of the compressed tissue (8, 12) undergoing necrosis. While only two such latched states are shown herein, defined by the first and second latching chambers (174, 176), it will be appreciated that the spike member (142) and/or the latching arms (144) may be suitably modified as desired to provide additional latched states. Additionally, while the first and second latching members of this version are shown in the form of a spike member (142) defining a male latching component, and latching arms (144) defining a female latching component, respectively, it will be appreciated that the latching members may be configured in various alternative forms and quantities suitable to provide multiple, progressive latched states between the first and second device halves (122, 124).

Figure 13A:
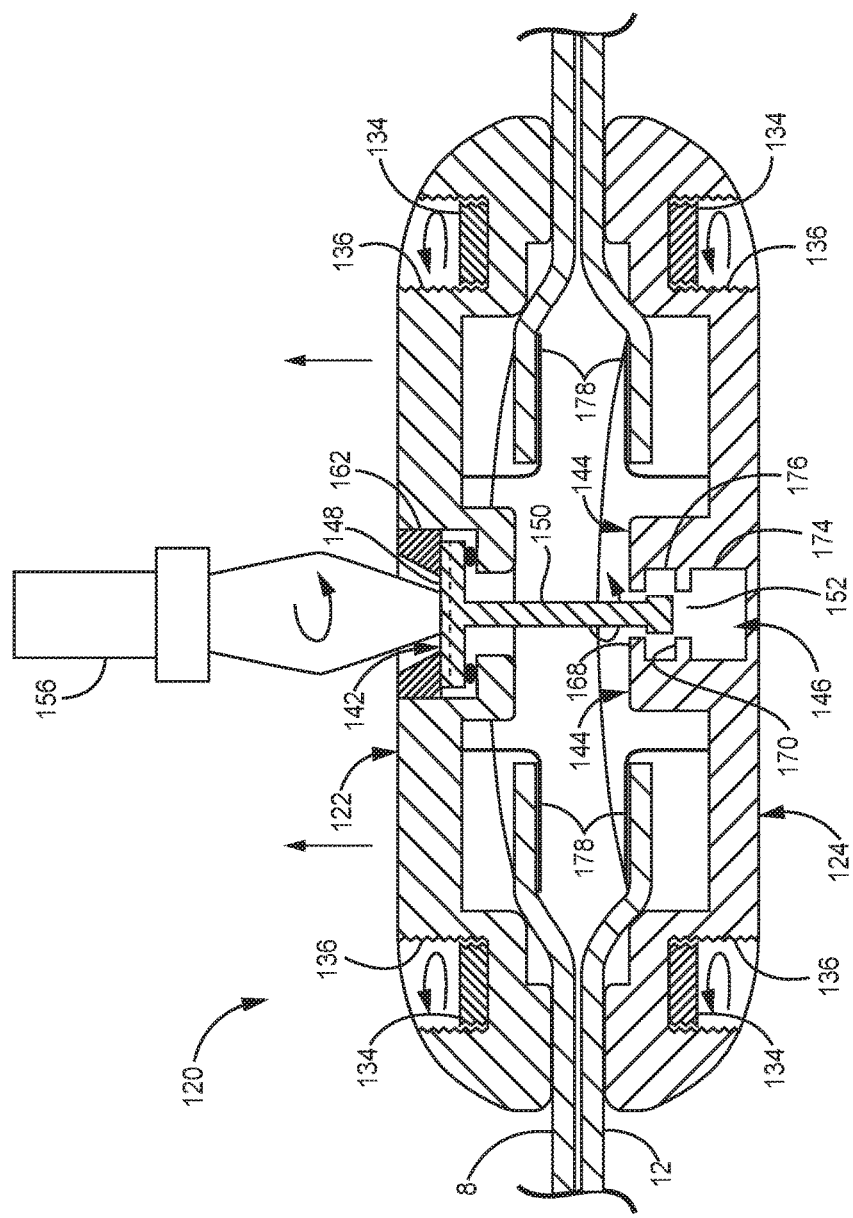
FIG. 13A depicts a side cross-sectional view of the tissue compression device of FIG. 9, showing rotation of the spike member and magnetic members for decoupling the first and second device halves.
Figure 13B:
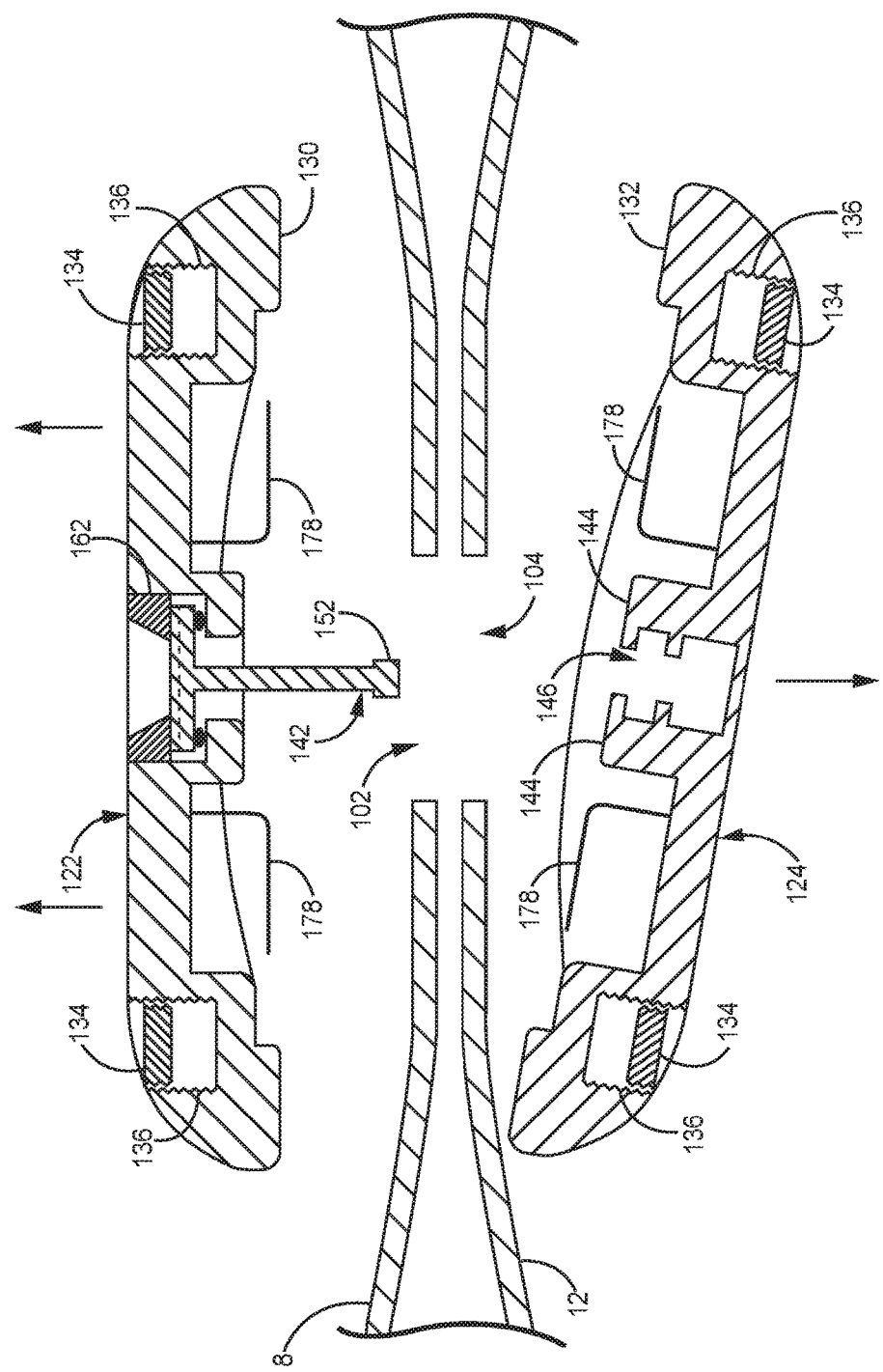
FIG. 13B depicts a side cross-sectional view of the tissue compression device of FIG. 9, showing the first and second device halves after having been decoupled from one another and disengaged from the sidewalls of the duodenum and ileum.

FIGS. 13A and 13B show an exemplary decoupling (or "bail-out") procedure in which the first and second device halves (122, 124) of the tissue compression device (120) are separated from one another after the device halves (122, 124) have been deployed within a patient and before the formation of an anastomosis. As shown in FIG. 13A, a tool (156) is inserted into the tool engagement recess (154) (see FIG. 12A) on the spike member head (148), and is manipulated to rotate the spike member (142) and its barbed tip (152) approximately ninety degrees in either direction, relative to the first device half (122), to thereby disengage the barbed tip (152) from the latching fingers (168, 170). In other versions, the latching fingers (168, 170) and/or the barbed tip (152) may be shaped in various alternative manners as desired so that a greater or lesser degree of rotation is required to disengage the barbed tip (152).

In addition to the spike member (142), one or more of the magnetic members (134) may be rotated within their threaded sockets (136), via their tool engagement recesses (140) (see FIGS. 9 and 11A), to advance the magnetic members (134) away from the device axis. This axial repositioning of the magnetic members (134) within their sockets (136) increases a distance between attracting pairs of the magnetic members (134), and thus decreases the magnetic force drawing the device halves (122, 124) together. As a result, the unlatched device halves (122, 124) may be separated more easily. As shown in FIG. 13B, the unlatched device halves (122, 124) are then separated from one another and removed from the patient or otherwise allowed to pass downstream through the gastrointestinal tract (2). Alternatively, the unlatched device halves (122, 124) may be repositioned and then reinstalled within the gastrointestinal tract (2).

FIGS. 14A and 14B show another exemplary alternative tissue compression device (180) for forming an anastomosis, such as a side-by-side anastomosis. The device (180) is similar in structure and function to device (120) described above, as indicated by like reference numerals. In addition to the features of device (120), device (180) further includes a compressible member (182) supported by the first device half (122) and arranged between the mating surfaces (130, 132) of the device (180) when the device halves (122, 124) are assembled. As shown, the first device half (122) may include a channel (184) formed in its mating surface (130), and in which a t-shaped base portion (186) of the compressible member (182) is releasably seated. The compressible member (182) may extend continuously about the mating surfaces (130, 132). In other versions, the compressible member (182) may be similarly mounted to the second device half (124).

As shown in FIG. 14B, the compressible member (182) is configured to compress into a flattened state between the mating surfaces (130, 132) of the device halves (122, 124) as the halves (122, 124) are drawn together by the magnetic members (134). As the compressible member (182) flattens, it exerts a compressive force on the tissue layers (8, 12) positioned between the device halves (122, 124). The compressible member (182) ensures that a compressive force is maintained on the tissue layers (8, 12) throughout an entire range of travel of the barbed tip (152) of the spike member (142) within the latching socket (146). Various suitable materials and configurations that may be used to form compressible member (182) will be apparent to those of ordinary skill in the art in view of the teachings herein.

Figure 15:
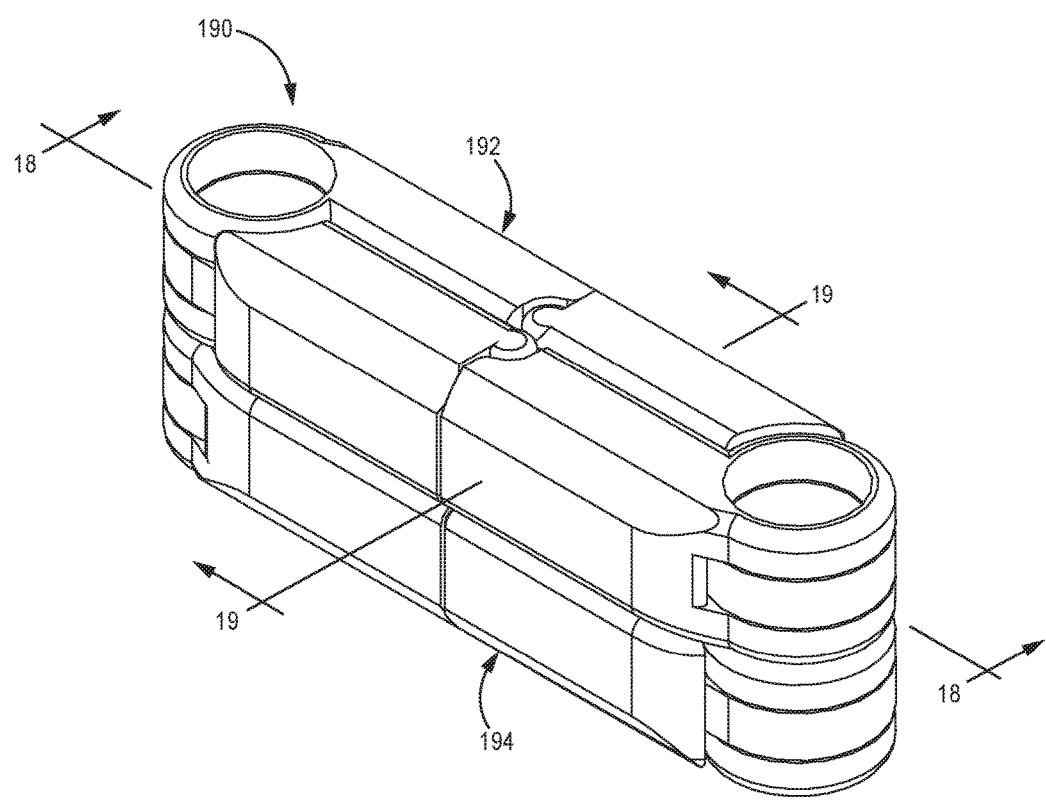
FIG. 15 depicts a perspective view of another exemplary tissue compression device for forming an anastomosis, the device shown in a collapsed state with first and second device halves latched together.
Figure 16:
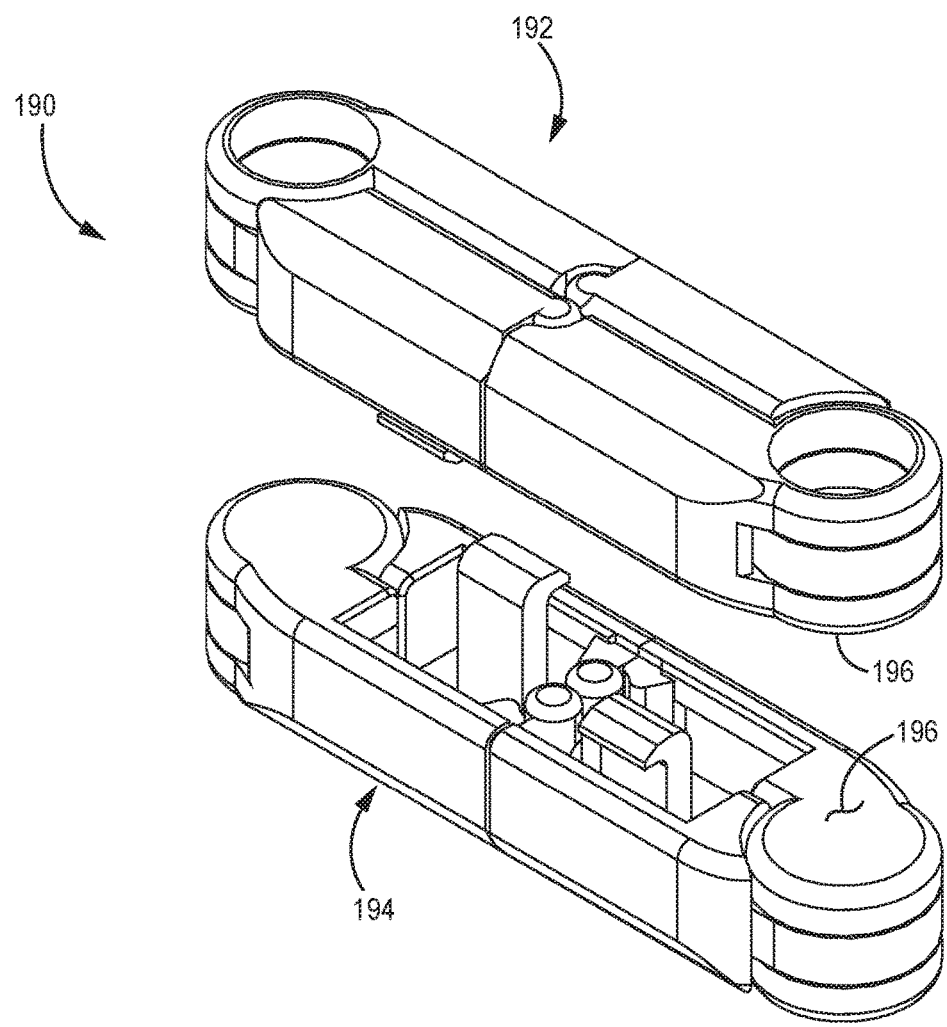
FIG. 16 depicts a disassembled perspective view of the tissue compression device of FIG. 15, showing the first and second device halves separated from each other.

D. Exemplary Alternative Anastomosis Tissue Compression Device Having Latching Mechanism and Pivotable Links FIGS. 15 and 16 show another exemplary tissue compression device (190) for forming an anastomosis, such as a side-by-side anastomosis. The device (190) includes a first device half (192) and a second device half (194), which may be identical in structure, and which are configured to combine at mating surfaces (196) to compress tissue therebetween.

As best shown in FIGS. 17A and 17B, each device half (192, 194) includes four links pivotably coupled with one another at four pivot joints. More specifically, a first link (198) is pivotably coupled with a second link (200) at a first end pivot joint (202). A third link (204) is pivotably coupled with a fourth link (206) at a second end pivot joint (208). Furthermore, the first and third links (198, 204) are pivotably coupled with one another at a first side medial pivot joint (210), and the second and fourth links (200, 206) are pivotably coupled with one another at a second side medial pivot joint (212). The links (198, 200, 204, 206) of each device half (192, 194) are pivotable relative to one another, about the pivot joints (202, 208, 210, 212), to transition the device half (192, 194) between a collapsed state, shown in FIG. 17A, and an expanded state, shown in FIG. 17B. Though not shown, each device half (192, 194) may further include a resilient member that biases the device half (192, 194) toward the expanded state, for example as disclosed in U.S. patent application Ser. No. 15/298,816, published as U.S. Pub. No. 2017/0035425 on Feb. 9, 2017, incorporated by reference above.

Figure 18:
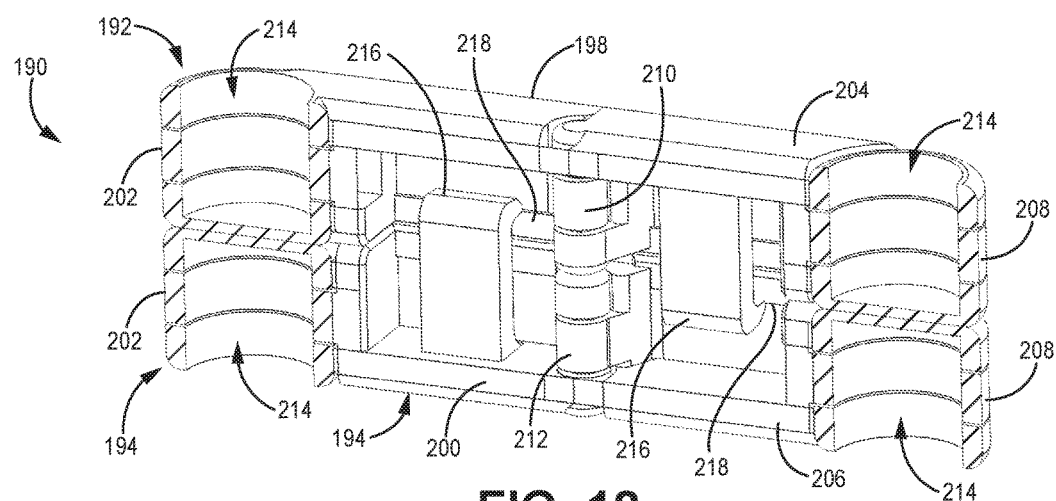
FIG. 18 depicts a perspective longitudinal cross-sectional view of the tissue compression device of FIG. 15, taken along section line 18-18 of FIG. 15, showing latching members of the first and second device halves in a latched state.

As shown best in FIG. 18, each of the end pivot joints (202, 208) may include a socket (214) configured to receive a magnetic member (not shown) therein. When the first and second device halves (192, 194) are positioned such that their mating surfaces (196) confront one another, the magnetic members draw the two device halves (192, 194) together and compress tissue therebetween to form an anastomosis, as generally described above.

The tissue compression device (190) further includes a latching mechanism configured to couple the first and second device halves (192, 194) together and reinforce the magnetic coupling provided by the magnetic members. The latching mechanism is shown in the form of a plurality of latching arms (216) and a corresponding plurality of ridges (218). As best shown in FIGS. 17A-19, each device half (192, 194) includes a first latching arm (216) extending from a base wall of the second link (200) and a second latching arm (216) extending from a base wall of the third link (204). Each latching arm (216) is shown extending transversely toward to a longitudinal axis of the device half (192, 194), and beyond an upper edge of the respective link (200, 204). Each latching arm (216) may be oriented to face away from the device half axis. The ridges (218) extend axially along the inner faces of at least the first link (198) and the fourth link (206), and may also extend along inner faces of the second and third links (200, 204).

Figure 19:
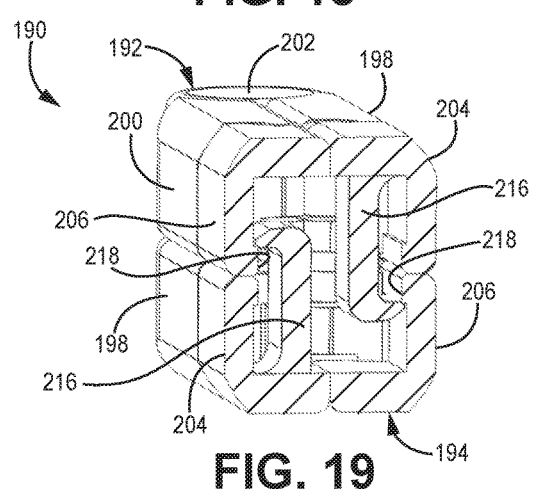
FIG. 19 depicts a perspective transverse cross-sectional view of the tissue compression device of FIG. 15, taken along section line 19-19 of FIG. 15, showing the latching members in a latched state.

As shown in FIGS. 18 and 19, each latching arm (216) of each device half (192, 194) is configured to lockingly engage a respective ridge (218) formed on the opposing device half (192, 194). In particular, as the device halves (192, 194) are drawn together magnetically, the latching arms (216) may resiliently deflect inwardly toward the longitudinal axis of the device half (192, 194), and then spring back to their relaxed states to hook onto the ridges (218) and establish a snap-fit engagement between the device halves (192, 194). While FIGS. 18 and 19 show the device halves (192, 194) lockingly coupled while in their collapsed states, it will be appreciated that the device halves (192, 194) may be similarly coupled while in their expanded states. The latching arms (216) may be released from the ridges (218) by prying the latching arms (216) inwardly with a tool (not shown) inserted through a central opening defined between the first and second side medial pivot joints (210, 212) when the device (190) is in an expanded state.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A tissue compression device for forming an anastomosis between first and second anatomical structures, the device comprising: (a) a first device portion having a first magnetic member; (b) a second device portion having a second magnetic member, wherein the first and second magnetic members are configured to magnetically draw together the first and second device portions in a confronting relationship to compress tissue positioned therebetween; and (c) a latching mechanism configured to couple the first device portion with the second device portion when the device portions are magnetically drawn together, wherein the latching mechanism includes: (i) a first latching member extending from the first device portion, and (ii) a second latching member extending from the second device portion, wherein the first and second latching members are configured to lockingly engage and thereby couple the first device portion with the second device portion.

Example 2

The tissue compression device of Example 1, wherein the latching mechanism is releasable.

Example 3

The tissue compression device of any one or more of Examples 1 through 2, wherein the latching mechanism is positioned inwardly of an outer periphery of the device.

Example 4

The tissue compression device of any one or more of Examples 1 through 3, wherein the first and second latching members extend toward a longitudinal axis of the device.

Example 5

The tissue compression device of any one or more of Examples 1 through 4, wherein the first latching member includes a male component and the second latching member includes a female component configured to receive and retain the male component.

Example 6

The tissue compression device of any one or more of Examples 1 through 5, wherein the first magnetic member includes a barbed tip and the second magnetic member includes a bore, wherein the barbed tip is configured to pierce through tissue clamped between the first and second device portions when the device portions are magnetically drawn together, and wherein the bore is configured to receive and retain the barbed tip therein.

Example 7

The tissue compression device of any one or more of Examples 1 through 6, wherein the first latching member includes a spike member extending toward a longitudinal axis of the compression device and having a distal tip, and the second latching member includes a latching socket configured to receive and retain the distal tip therein when the first and second device portions are magnetically drawn together, wherein the engagement of the spike member with the latching socket is configured to maintain the device portions in coupling engagement.

Example 8

The tissue compression device of Example 7, wherein the distal tip of the spike member is movable within the latching socket between a first position and a second position spaced from the first position, wherein the distal tip is configured to advance from the first position to the second position as the device portions are magnetically drawn together, and the distal tip is hindered from receding from the second position to the first position.

Example 9

The tissue compression device of any one or more of Examples 7 through 8, wherein the latching socket includes a first chamber and a second chamber spaced from the first chamber in a direction away from the device axis, wherein the first and second chambers are configured to receive and retain the distal tip of the spike member therein, and wherein the first and second chambers define the first and second positions, respectively, of the distal tip.

Example 10

The tissue compression device of any one or more of Examples 7 through 9, wherein the spike member is selectively rotatable relative to the first and second device portions to disengage the latching socket and thereby enable decoupling of the first and second device portions.

Example 11

The tissue compression device of any one or more of Examples 1 through 10, wherein at least one of the magnetic members is received within a socket in which the magnetic member is selectively movable in a direction away from an opposing magnetic member of the other device portion to thereby lessen a magnetic attraction force between the first and second device portions and facilitate decoupling of the device portions.

Example 12

The tissue compression device of any one or more of Examples 1 through 11, further comprising a compressible member arranged between mating surfaces of the first and second device portions, wherein the compressible member is configured to engage a layer of tissue positioned between the device portions, and wherein the compressible member is configured to compress as the device portions are magnetically drawn together.

Example 13

The tissue compression device of any one or more of Examples 1 through 12, wherein each of the first and second device portions further includes at least one retaining clip configured to engage a layer of tissue for holding the device in position while the tissue is compressed between the device portions.

Example 14

The tissue compression device of any one or more of Examples 1 through 13, wherein the first device portion defines a first half of the device and the second device portion defines a second half of the device.

Example 15

The tissue compression device of any one or more of Examples 1 through 14, wherein the first device portion includes a first recessed base wall and the second device portion includes a second recessed base wall, and the first and second device portions combine to define a closed interior cavity bounded by the first and second recessed base walls.

Example 16

The tissue compression device of any one or more of Examples 1 through 15, wherein the first device portion includes a first mating surface having a first contour, and the second device portion includes a second mating surface having a second contour configured to complement the first contour when the first and second device portions are positioned in confronting relationship for compressing tissue therebetween.

Example 17

A tissue compression device for forming an anastomosis between first and second anatomical structures, the device comprising: (a) a first device portion; (b) a second device portion configured to mate with the first device portion; (c) a first magnetic member supported by the first device portion; (d) a second magnetic member supported by the second device portion, wherein the magnetic members are configured to magnetically draw together the first and second device portions to compress tissue positioned therebetween; and (e) a latching mechanism configured to couple the first device portion with the second device portion when the device portions are magnetically drawn together, wherein the latching mechanism includes: (i) a first latching member fixedly coupled to the first device portion, and (ii) a second latching member fixedly coupled to the second device portion, wherein at least one of the first or second latching members is configured to resiliently deflect when engaging the other of the first or second latching members.

Example 18

The tissue compression device of Example 17, wherein the latching mechanism is positioned inwardly of an outer periphery of the device.

Example 19

A tissue compression device for forming an anastomosis between first and second anatomical structures, the device comprising: (a) a unitary first device half; (b) a unitary second device half configured to mate with the first device half to define a rounded outer periphery of the device; (c) a first magnetic member supported by the first device half; (d) a second magnetic member supported by the second device half, wherein the magnetic members are configured to magnetically draw together the first and second device halves to compress tissue positioned therebetween; and (e)

a latching mechanism configured to couple the first device portion with the second device portion when the device portions are magnetically drawn together.

Example 20

The tissue compression device of Example 19, wherein the latching mechanism is positioned inwardly of the outer periphery of the device.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the devices may be disassembled, and any number of the particular pieces or parts of the devices may be selectively replaced or removed in any combination. Upon cleaning and/or replacement of particular parts, some versions of the devices may be reassembled for subsequent use either at a reconditioning facility, or by a user immediately prior to a procedure. Those skilled in the art will appreciate that reconditioning of a devices may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A tissue compression device for forming an anastomosis between first and second anatomical structures, the device comprising:
   (a) a first device portion having a first magnetic member;
   (b) a second device portion having a second magnetic member, wherein the first and second magnetic members are configured to magnetically draw together the first and second device portions in a confronting relationship to compress tissue positioned therebetween; and
   (c) a latching mechanism configured to couple the first device portion with the second device portion when the device portions are magnetically drawn together, wherein the latching mechanism includes:
      (i) a first latching member extending from the first device portion, and
      (ii) a second latching member extending from the second device portion,
      wherein the first and second latching members are configured to lockingly engage and thereby couple the first device portion with the second device portion,
      wherein the first latching member is selectively rotatable relative to the second latching member to release the first device portion from the second device portion.

2. The tissue compression device of claim 1, wherein the latching mechanism is releasable.

3. The tissue compression device of claim 1, wherein the latching mechanism is positioned inwardly of an outer periphery of the device.

4. The tissue compression device of claim 1, wherein the first and second latching members extend toward a longitudinal axis of the device.

5. The tissue compression device of claim 1, wherein the first latching member includes a male component and the second latching member includes a female component configured to receive and retain the male component.

6. The tissue compression device of claim 1, wherein the first magnetic member includes a barbed tip and the second magnetic member includes a bore, wherein the barbed tip is configured to pierce through tissue clamped between the first and second device portions when the device portions are magnetically drawn together, and wherein the bore is configured to receive and retain the barbed tip therein.

7. The tissue compression device of claim 1, wherein the first latching member includes a spike member extending toward a longitudinal axis of the compression device and having a distal tip, and the second latching member includes a latching socket configured to receive and retain the distal tip therein when the first and second device portions are magnetically drawn together,
wherein the engagement of the spike member with the latching socket is configured to maintain the device portions in coupling engagement.

8. The tissue compression device of claim 7, wherein the distal tip of the spike member is movable within the latching socket between a first position and a second position spaced from the first position,
wherein the distal tip is configured to advance from the first position to the second position as the device portions are magnetically drawn together, and the distal tip is hindered from receding from the second position to the first position.

9. The tissue compression device of claim 7, wherein the latching socket includes a first chamber and a second chamber spaced from the first chamber in a direction away from the device axis, wherein the first and second chambers are configured to receive and retain the distal tip of the spike member therein, and wherein the first and second chambers define the first and second positions, respectively, of the distal tip.

10. The tissue compression device of claim 7, wherein the spike member is selectively rotatable relative to the first and second device portions to disengage the latching socket and thereby enable decoupling of the first and second device portions.

11. The tissue compression device of claim 1, wherein at least one of the magnetic members is received within a socket in which the magnetic member is selectively movable in a direction away from an opposing magnetic member of the other device portion to thereby lessen a magnetic attraction force between the first and second device portions and facilitate decoupling of the device portions.

12. The tissue compression device of claim 1, further comprising a compressible member arranged between mating surfaces of the first and second device portions, wherein the compressible member is configured to engage a layer of tissue positioned between the device portions, and wherein the compressible member is configured to compress as the device portions are magnetically drawn together.

13. The tissue compression device of claim 1, wherein each of the first and second device portions further includes at least one retaining clip configured to engage a layer of tissue for holding the device in position while the tissue is compressed between the device portions.

14. The tissue compression device of claim 1, wherein the first device portion defines a first half of the device and the second device portion defines a second half of the device.

15. The tissue compression device of claim 1, wherein the first device portion includes a first recessed base wall and the second device portion includes a second recessed base wall, and the first and second device portions combine to define a closed interior cavity bounded by the first and second recessed base walls.

16. The tissue compression device of claim 1, wherein the first device portion includes a first mating surface having a first contour, and the second device portion includes a second mating surface having a second contour configured to complement the first contour when the first and second device portions are positioned in confronting relationship for compressing tissue therebetween.

17. A tissue compression device for forming an anastomosis between first and second anatomical structures, the device comprising:
(a) a first device portion comprising:
(i) a first magnetic member having a barbed tip, and
(ii) a first latching member; and
(b) a second device portion comprising:
(i) a second magnetic member having a bore, and
(ii) a second latching member,
wherein the first and second magnetic members are configured to magnetically draw together the first and second device portions in a confronting relationship to compress tissue positioned therebetween,
wherein the barbed tip of the first magnetic member is configured to pierce through the tissue, wherein the bore of the second magnetic member is configured to receive and retain the barbed tip therein,
wherein the first and second latching members are configured to lockingly engage one another when the first and second device portions are magnetically drawn together.

18. The tissue compression device of claim 17, wherein the first magnetic member is movable within an opening of the first device portion.

19. A tissue compression device for forming an anastomosis between first and second anatomical structures, the device comprising:
(a) a first device portion comprising:
(i) a first magnetic member, and
(ii) a first latching member; and
(b) a second device portion comprising:
(i) a socket,
(ii) a second magnetic member arranged within the socket, and
(iii) a second latching member,
wherein the first and second magnetic members are configured to magnetically draw together the first and second device portions in a confronting relationship to compress tissue positioned therebetween,
wherein the first and second latching members are configured to lockingly engage one another when the first and second device portions are magnetically drawn together,
wherein the second magnetic member is selectively movable within the socket in a direction away from the first magnetic member to lessen a magnetic attraction force between the first and second magnetic members and thereby facilitate decoupling of the first and second device portions.

20. The tissue compression device of claim 19, wherein the second magnetic member is threadedly engaged with the socket of the second device portion.

* * * * *